US011980473B2

(12) United States Patent
Berry et al.

(10) Patent No.: US 11,980,473 B2
(45) Date of Patent: May 14, 2024

(54) SEIZURE ONSET ZONE LOCALIZATION

(71) Applicants: Brent M. Berry, Rochester, MN (US);
Gary C. Sieck, Rochester, MN (US);
Gregory A. Worrell, Rochester, MN
(US); Benjamin H. Brinkmann,
Byron, MN (US); **Yogatheesan
Varatharajah, Urbana, IL (US); Vaclav
Kremen**, Rochester, MN (US);
Ravishankar Krishnan Iyer,
Champaign, IL (US); **Zbigniew
Kalbarczyk, Urbana, IL (US); Jan
Cimbalnik**, Brno (CZ)

(72) Inventors: Brent M. Berry, Rochester, MN (US);
Gary C. Sieck, Rochester, MN (US);
Gregory A. Worrell, Rochester, MN
(US); Benjamin H. Brinkmann,
Byron, MN (US); **Yogatheesan
Varatharajah, Urbana, IL (US); Vaclav
Kremen**, Rochester, MN (US);
Ravishankar Krishnan Iyer,
Champaign, IL (US); **Zbigniew
Kalbarczyk, Urbana, IL (US); Jan
Cimbalnik**, Brno (CZ)

(73) Assignees: **Mayo Foundation for Medical
Education and Research**, Rochester,
MN (US); **The Board of Trustees of
the University of Illinois and St.
Anne's University Hospital Brno**,
Urbana, IL (US)

( * ) Notice: Subject to any disclaimer, the term of this patent is extended or adjusted under 35 U.S.C. 154(b) by 514 days.

(21) Appl. No.: 16/616,771

(22) PCT Filed: May 25, 2018

(86) PCT No.: PCT/US2018/034703
§ 371 (c)(1),
(2) Date: Nov. 25, 2019

(87) PCT Pub. No.: WO2018/218174
PCT Pub. Date: Nov. 29, 2018

(65) Prior Publication Data
US 2020/0178832 A1 Jun. 11, 2020

Related U.S. Application Data

(60) Provisional application No. 62/511,239, filed on May 25, 2017.

(51) Int. Cl.
*A61B 5/369* (2021.01)
*A61B 5/00* (2006.01)
*A61B 5/07* (2006.01)

(52) U.S. Cl.
CPC .............. *A61B 5/369* (2021.01); *A61B 5/076* (2013.01); *A61B 5/4094* (2013.01); *A61B 5/725* (2013.01)

(58) Field of Classification Search
CPC ....... A61B 5/369; A61B 5/076; A61B 5/4094; A61B 5/725
See application file for complete search history.

(56) References Cited

U.S. PATENT DOCUMENTS 7,282,030 B2  10/2007  Frei et al.
8,543,199 B2 *  9/2013  Snyder ................ A61B 5/0205
                                                      600/545

(Continued)

FOREIGN PATENT DOCUMENTS

WO  WO 2016/200952  12/2016

OTHER PUBLICATIONS

Extended European Search Report in European Application No. 18805187.4 dated Mar. 26, 2020, 14 pages.

(Continued)

*Primary Examiner* — Kaylee R Wilson

*Assistant Examiner* — Severo Antonio P Lopez
(74) *Attorney, Agent, or Firm* — Fish & Richardson P.C.

(57) ABSTRACT

This specification discloses systems, methods, devices, and other techniques for determining the location of a seizure-generating region of the brain of a mammal.

19 Claims, 21 Drawing Sheets

(56) References Cited

U.S. PATENT DOCUMENTS

| | | | | |
|---|---|---|---|---|
| 2007/0043402 | A1* | 2/2007 | Echauz | A61B 5/4094 |
| | | | | 607/45 |
| 2008/0183076 | A1* | 7/2008 | Witte | A61B 5/4064 |
| | | | | 600/438 |
| 2010/0302270 | A1* | 12/2010 | Echauz | A61B 5/4094 |
| | | | | 345/589 |
| 2014/0094710 | A1* | 4/2014 | Sarma | A61B 5/369 |
| | | | | 600/544 |
| 2015/0038870 | A1* | 2/2015 | Yoo | H03H 17/0248 |
| | | | | 330/9 |
| 2015/0099962 | A1 | 4/2015 | Weiss et al. | |

OTHER PUBLICATIONS

International Preliminary Report on Patentability in International Application No. PCT/US2018/034703 dated Nov. 26, 2019, 10 pages.
International Search Report & Written Opinion in International Application No. PCT/US2018/034703 dated Aug. 21, 2018, 18 pages.
Urigüen and Garcia-Zapirain, "EEG artifact removal—state-of-the-art and guidelines," Journal of neural engineering, 12(3):031001, Apr. 2015.
Varatharajah et al., "Inter-ictal seizure onset zone localization using unsupervised clustering and bayesian filtering," In 2017 8th International IEEE/EMBS Conference on Neural Engineering (NER), (pp. 533-539). IEEE, My\ay 2017.
Alvarado-Rojas et al., "Slow modulations of high-frequency activity (40-140 [emsp14] hz) discriminate preictal changes in human focal epilepsy," Sci. Reports, Apr. 1, 2014, 4:4545, 9 pages.
Amiri et al., "Phase-Amplitude Coupling Is Elevated in Deep Sleep and in the Onset Zone of Focal Epileptic Seizures," Front. Hum. Neuroscience, Aug. 3, 2016, 10:387, 12 pages.
Andrzejak et al., "Seizure prediction: Any better than chance?" Clin. Neurophysiology, Aug. 2009, 120(8):1465-1478.
Balach et al., "Comparison of Algorithms for Detection of High Frequency Oscillations in Intracranial EEG," Presented at Proceedings of 2014 IEEE International Symposium on Medical Measurements and Applications, Lisboa, Portugal, Jun. 11-12, 2014, 4 pages.
Ben-Ari, "Physiologic and Pathologic Oscillations," Trends Neurosciences, Jul. 1, 2007, 30(7):307-308.
Blanco et al., "Comparison of frequency bands using spectral entropy for epileptic seizure prediction," ISRN, May 25, 2013, 2013:287327, 5 pages.
Blanco et al., "Unsupervised classification of high-frequency oscillations in human neocortical epilepsy and control patients," J. Neurophysiology, Sep. 1, 2010, 104(5):2900-2912.
Bragin et al., "High-frequency oscillations in human brain," Hippocampus, Apr. 15, 1999, 9(2):137-142.
Brinkmann et al., "Forecasting seizures using intracranial EEG measures and SVM in naturally occurring canine epilepsy," PLoS One, Aug. 4, 2015, 10(8):e0133900, 12 pages.
Brodie et al., "Staged approach to epilepsy management," Neurology, Apr. 23, 2002, 58(8 Suppl 5):S2-S8.
Burnos et al., "Human intracranial high frequency oscillations (HFOs) detected by automatic time-frequency analysis," PLoS One, Apr. 10, 2014, 9(4):e94381, 12 pages.
Buzsáki et al., "Emergence and propagation of interictal spikes in the subcortically denervated hippocampus," Hippocampus, Apr. 1991, 1(2):163-180.
Canolty et al., "High gamma power is phase-locked to theta oscillations in human neocortex," Science, Sep. 15, 2006, 313(5793):1626-1628.
Chaibi et al., "A comparaison of methods for detection of high frequency oscillations (HFOs) in human intacerberal EEG recordings," Am. J. Sig. Processing, 2013, 3(2):25-34.
Cimbalnik et al., "Interictal high-frequency oscillations in focal human epilepsy," Curr. Opin. Neurology, Apr. 2016, 29(2):175-181.
Colgin, "Rhythms of the hippocampal network," Nat. Rev. Neuroscience, Mar. 10, 2016, 17(4):239-249.
D'Alessandro et al., "Epileptic Seizure Prediction Using Hybrid Feature Selection over Multiple Intracranial EEG Electrode Contacts: A Report of Four Patients," IEEE Trans. Biomed. Engineering, May 2003, 50(5):603-615.
DiLorenzo et al., "Chronic unlimited recording electrocorticography-guided resective epilepsy surgery: technology-enabled enhanced fidelity in seizure focus localization with improved surgical efficacy," J. Neurosurgery, Mar. 21, 2014, 120(6):1402-1414.
Edakawa et al., "Detection of Epileptic Seizures Using Phase-Amplitude Coupling in Intracranial Electroencephalography," Sci. Reports, May 5, 2016, 6(1):25422, 8 pages.
Elsharkawy et al., "Long-term outcome of lesional posterior cortical epilepsy surgery in adults," J. Neurol. Neurosurg. Psychiatry, Jul. 2009, 80(7):773-780.
Engel Jr., "High-Frequency Oscillations: What Is Normal and What Is Not?," Epilepsia, Apr. 2009, 50(4):598-604.
Ferree et al., "Power-law scaling in human EEG: Relation to Fourier power spectrum," Neurocomputing, Jun. 2003, 52-54:755-761.
Fisch et al., "The role of quantitative topographic mapping or 'neurometrics' in the diagnosis of psychiatric and neurological disorders: the cons," Electroencephalogr. Clin. Neurophysiology, Jul. 1989, 73(1):5-9.
Gardner et al., "Human and automated detection of high-frequency oscillations in clinical intracranial EEG recordings," Clin. Neurophysiology, May 2007, 118(5):1134-1143.
Geertsema et al., "Automated Seizure Onset Zone Approximation Based on Nonharmonic High-Frequency Oscillations in Human Interictal Intracranial EEGs," Int. J. Neural Systems, Aug. 2015, 25(5):1550015, 18 pages.
Graef et al., "Automatic Ictal HFO Detection for Determination of Initial Seizure Spread," Annu. Int. Conf. IEEE Eng. Med. Biol. Society, Jul. 2013, 2013:2096-2099.
Gritsch et al., "Automatic Detection of the Seizure Onset Zone Based on Ictal EEG," Annu. Int. Conf. IEEE Eng. Med. Biol. Society, Aug. 2011, 2011:3901-3904.
Gump et al., "Seizure control after subtotal lesional resection," Neurosurg. Focus, Jun. 2013, 34(6):E1, 5 pages.
Hauf et al., "Localizing Seizure-Onset Zones in Presurgical Evaluation of Drug-Resistant Epilepsy by Electroencephalography/fMRI: Effectiveness of Alternative Thresholding Strategies," AJNR Am. J. Neuroradiology, Apr. 26, 2012, 33(9):1818-1824.
Höller et al., "High-Frequency Oscillations in Epilepsy and Surgical Outcome. A Meta-Analysis," Front. Human Neuroscience, Oct. 20, 2015, 9:574, 14 pages.
Jacobs et al., "High-Frequency Electroencephalographic Oscillations Correlate with Outcome of Epilepsy Surgery," Ann. Neurology, Feb. 2010, 67(2):209-220.
Jacobs et al., "Interictal High-Frequency Oscillations (80-500 Hz) Are an Indicator of Seizure Onset Areas Independent of Spikes in the Human Epileptic Brain," Epilepsia, Nov. 2008, 49(11):1893-1907.
Jenks, "The data model concept in statistical mapping," Int. Yearbook Cartography, 1967, 7(1):186-190.
Jensen et al., "Cross-frequency coupling between neuronal oscillations," Trends Cogn. Sciences, Jun. 4, 2007, 11(7):267-269.

(56) References Cited

OTHER PUBLICATIONS

Kalamangalam et al., "An interictal eeg spectral metric for temporal lobe epilepsy lateralization," Epilepsy Research, Sep. 16, 2014, 108(10):1748-1757.
Kremen et al., "Behavioral State Classification in Epileptic Brain Using Intracranial Electrophysiology," J. Neural Engineering, Jan. 4, 2017, 14(2):26001, 9 pages.
Lee et al., "Diagnostic outcome of surgical revision of intracranial electrode placements for seizure localization," J. Clin. Neurophysiology, Jun. 2014, 31(3):199-202.
Lee, "Surgical approaches in nonlesional neocortical epilepsy," J. Epilepsy Research, Dec. 30, 2011, 1(2):47-51.
Liu et al., "Exploring the Time-frequency Content of High Frequency Oscillations for Automated Identification of Seizure Onset Zone in Epilepsy," J. Neural Engineering, Feb. 29, 2016, 13(2):26026, 15 pages.
Lüders et al., "The epileptogenic zone: general principles," Epileptic Disorders, Aug. 2006, 8(S2):S1-S9.
Marsh et al., "Interictal EEG spikes identify the region of electrographic seizure onset in some, but not all, pediatric epilepsy patients," Epilepsia, Apr. 2010, 51(4):592-601.
Matsumoto et al., "Pathological and Physiological High-Frequency Oscillations in Focal Human Epilepsy," J. Neurophysiology, Aug. 7, 2013, 110(8):1958-1964.
Nair et al., "On Entropy for Mixtures of Discrete and Continuous Variables," arXiv, Jul. 14, 2006, arXiv:cs/0607075v1, 10 pages.
Noe et al., "Long-term Outcomes After Nonlesional Extratemporal Lobe Epilepsy Surgery," JAMA Neurology, Aug. 2013, 70(8):1003-1008.
Nonoda et al., "Interictal High-Frequency Oscillations Generated by Seizure Onset and Eloquent Areas May Be Differentially Coupled with Different Slow Waves," Clin. Neurophysiology, Apr. 6, 2016, 127(6):2489-2499.
Papadelis et al., "Interictal High Frequency Oscillations Detected with Simultaneous Magnetoencephalography and Electroencephalography as Biomarker of Pediatric Epilepsy," J. Vis. Experiments, Dec. 6, 2016, 118:54883, 13 pages.
Schevon et al., "Spatial characterization of interictal high frequency oscillations in epileptic neocortex," Brain, Nov. 2009, 132(11):3047-3059.
Sinha et al., "Predicting Neurosurgical Outcomes in Focal Epilepsy Patients Using Computational Modelling," Brain, Dec. 23, 2016, 140(2):319-332.
Staba et al., "High-frequency oscillations recorded in human medial temporal lobe during sleep," Ann. Neurology, Jul. 2004, 56(1):108-115.
Staba et al., "Quantitative analysis of high-frequency oscillations (80-500 Hz) recorded in human epileptic hippocampus and entorhinal cortex," J. Neurophysiology, Oct. 2002, 88(4):1743-1752.
Staley et al., "Interictal spikes and epileptogenesis," Epilepsy Currents, Nov./Dec. 2006, 6(6):199-202.
Stead et al., "Microseizures and the spatiotemporal scales of human partial epilepsy," Brain, Sep. 2010, 133(9):2789-2797.
Tellez-Zenteno et al., "Long-term seizure outcomes following epilepsy surgery: a systematic review and meta-analysis, " Brain, May 2005, 128(5):1188-1198.
Varatharajah et al., "Seizure forecasting and the preictal state in canine epilepsy," Int. J. Neural Systems, Jun. 14, 2016, 27(1):1650046, 12 pages.
Von Ellenrieder et al., "Physiological and Pathological High-Frequency Oscillations Have Distinct Sleep-Homeostatic Properties," NeuroImage: Clinical, Feb. 24, 2017, 14:566-573.
Warren et al., "Synchrony in normal and focal epileptic brain: the seizure onset zone is functionally disconnected," J. Neurophysiology, Dec. 2010, 104(6):3530-3539.
Weiss et al., "Ictal High Frequency Oscillations Distinguish Two Types of Seizure Territories in Humans," Brain, Oct. 30, 2013, 136(12):3796-3808.
Wetjen et al., "Intracranial electroencephalography seizure onset patterns and surgical outcomes in nonlesional extratemporal epilepsy," J. Neurosurgery, Jun. 2009, 110(6):1147-1152.
Worrell et al., "High-frequency oscillations in human temporal lobe: Simultaneous microwire and clinical macroelectrode recordings," Brain, Apr. 2008, 131(4):928-937.
Ylinen et al., "Sharp wave-associated high-frequency oscillation (200 Hz) in the intact hippocampus: network and intracellular mechanisms," J. Neuroscience, Jan. 1995, 15(1 Pt 1):30-46.
Yun et al., "Prognostic factors in neocortical epilepsy surgery: multivariate analysis," Epilepsia, Mar. 2006, 47(3):574-579.
Zijlmans et al., "High-frequency oscillations as a new biomarker in epilepsy," Ann. Neurology, Feb. 2012, 71(2):169-178.
Barkmeier et al., "High inter-reviewer variability of spike detection on intracranial EEG addressed by an automated multi-channel algorithm," Clinical Neurophysiology, Jun. 2012, 123(6):1088-1095.
Blakely et al., "Localization and classification of phonemes using high spatial resolution electrocorticography (ECoG) grids," Proc. 30th Annual International Conference of the IEEE Engineering in Medicine and Biology Society, Aug. 20-24, 2008, 4964-4967.
Boser et al., "A training algorithm for optimal margin classifiers," Proc Fifth Annual Workshop on Computational Learning Theory, Jul. 1992, 144-152.
Bragin et al., "Interictal high-frequency oscillations (80-500 Hz) in the human epileptic brain: Entorhinal cortex," Ann Neurol, May 2002, 52:407-415.
Brinkmann et al., "Large-scale electrophysiology: Acquisition, compression, encryption, and storage of big data," Journal of Neuroscience Methods, May 2009, 180(1):185-192.
Burkholder et al., "Interictal scalp electroencephalography and intraoperative electrocorticography in magnetic resonance imaging-negative temporal lobe epilepsy surgery," JAMA Neurology, Apr. 2014, 71(6):702-709.
Canolty et al., "Multivariate phase-amplitude crossfrequency coupling in neurophysiological signals," IEEE Transactions on Biomedical Engineering, Jan. 2012, 59(1):8-11.
Cherkassky et al., "Simple Method for Interpretation of High-Dimensional Nonlinear SVM Classification Models," DMIN, Jul. 2010, 267-272.
Cortes et al., "Support-vector networks," Machine Learning, Mar. 1995, 20(3):273-297.
Crisler et al., "Sleep-stage scoring in the rat using a support vector machine," Journal of Neuroscience Methods, Mar. 2008, 168(2):524-534.
Engel Jr. et al., "Epilepsy biomarkers," Epilepsia, Aug. 2013, 54(Suppl, 4):61-69.
Esteva et al., "Dermatologist-level classification of skin cancer with deep neural networks," Nature, Feb. 2017, 542(7639):115-118.
Fisher et al., "Electrical brain stimulation for epilepsy," Nat Rev Neurol, May 2014, 10:261-270.
Gnatkovsky et al., "Biomarkers of epileptogenic zone defined by quantified stereo—EEG analysis," Epilepsia, Feb. 2014, 55(2):296-305.
Gulshan et al., "Development and validation of a deep learning algorithm for detection of diabetic retinopathy in retinal fundus photographs," JAMA, Dec. 2016, 316(22):2402-2410.
Hauf et al., "Localizing seizure-onset zones in presurgical evaluation of drug-resistant epilepsy by electroencephalography/fMRI: Effectiveness of alternative thresholding strategies," American Journal of Neuroradiology, Oct. 2012, 33(9):1818-1824.
Jirsch et al, "High-frequency oscillations during human focal seizures," Brain, Jun. 2006, 129(6):1593-1608.
Karoly et al., "Interictal spikes and epileptic seizures: Their relationship and underlying rhythmicity," Brain, Apr. 2016, 139(4):1066-1078.
Kucewicz et al., "Dissecting gamma frequency activity during human memory processing," Brain, May 2017, 140(5):1337-1350.
Kwan et al., "Early identification of refractory epilepsy," The New England Journal of Medicine, Feb. 2000, 342(5):314-319.
Leonardi et al., "The global burden of epilepsy," Epilepsia, Oct. 2002, 43(s6):21-25.

(56) References Cited

OTHER PUBLICATIONS

Luther et al., "The value of intraoperative electrocorticography in surgical decision making for temporal lobe epilepsy with normal MRI," Epilepsia, May 2011, 52(5):941-948.
Malow et al., "Interictal spiking increases with sleep depth in temporal lobe epilepsy," Epilepsia, Dec. 1998, 39(12):1309-1316.
Miller et al., "Decoupling the cortical power spectrum reveals real-time representation of individual finger movements in humans," Journal of Neuroscience, Mar. 2009, 29(10):3132-3137.
Pail et al., "Frequency-independent characteristics of high-frequency oscillations in epileptic and non-epileptic regions," Clinical Neurophysiology, Jan. 2017, 128(1):106-114.
Pearce et al., "Temporal changes of neocortical high frequency oscillations in epilepsy," J Neurophysiol, Sep. 2013, 110(5):1167-1179.
Refaeilzadeh et al., "Cross-validation," Encyclopedia of Database Systems, Springer US, 2009, 532-538.
Sammaritano et al., "Interictal spiking during wakefulness and sleep and the localization of foci in temporal lobe epilepsy," Neurology, Feb. 1991, 41:290-297.
Schwartz et al., "The predictive value of intraoperative electrocorticography in resections for limbic epilepsy associated with mesial temporal sclerosis," Neurosurgery, Feb. 1997, 40:302-309 (Abstract Only).
Tzallas et al., "Automatic seizure detection based on time-frequency analysis and artificial neural networks," Computational Intelligence and Neuroscience, Oct. 2007, 2007:80510, 13 pages.
Tzourio-Mazoyer et al., "Automated anatomical labeling of activations in SPM using a macroscopic anatomical parcellation of the MNI MRI single-subject brain," NeuroImage, Jan. 2002, 15:273-289.
Van 't Klooster et al., "High frequency oscillations in the intra-operative ECoG to guide epilepsy surgery ("The HFO Trial"): Study protocol for a randomized controlled trial," Trials, Sep. 2015, 16:422.

Van Gompel et al., "Electrocorticography-guided resection of temporal cavernoma: Is electrocorticography warranted and does it alter the surgical approach?" J Neurosurg, Jun. 2009, 110(6):1179-1185.
Van Gompel et al., "Intracranial electroencephalography with subdural grid electrodes: Techniques, complications, and outcomes," Neurosurgery, Sep. 2008, 63(3):498-505.
Varatharajah et al., "EEG-Graph: A factor-graph-based model for capturing spatial, temporal, and observational relationships in electroencephalograms," Advances in Neural Information Processing Systems, Jan. 2017, 30:5377-5386.
Wass et al., "The effects of remifentanil on epileptiform discharges during intraoperative electrocorticography in patients undergoing epilepsy surgery," Epilepsia, Oct. 2001, 42:1340-1344.
Weiss et al., "Ictal onset patterns of local field potentials, high frequency oscillations, and unit activity in human mesial temporal lobe epilepsy," Epilepsia, Jan. 2016, 57(1):111-121.
Weiss et al., "Seizure localization using ictal phase-locked high gamma: A retrospective surgical outcome study," Neurology, Jun. 2015, 84(23):2320-2328.
Wellmer et al., "Risks and benefits of invasive epilepsy surgery workup with implanted subdural and depth electrodes," Epilepsia, Aug. 2012, 53:1322-1332.
Worrell et al., "High-frequency oscillations and other electrophysiological biomarkers of epilepsy: Clinical studies," Biomarkers in Medicine, Oct. 2011, 5(5):557-566.
Worrell et al., "High-frequency oscillations and seizure generation in neocortical epilepsy," Brain, Jul. 2004, 127(7):1496-1506.
Worrell et al., "Recording and analysis techniques for high-frequency oscillations," Progress in Neurobiology, Sep. 2012, 98(3):265-278.
Wu et al., "Removing interictal fast ripples on electrocorticography linked with seizure freedom in children," Neurology, Nov. 2010, 75(19):1686-1694.

* cited by examiner

- Detected SOZ
- Detected non-SOZ
- Gold standard SOZ
- Bad channels

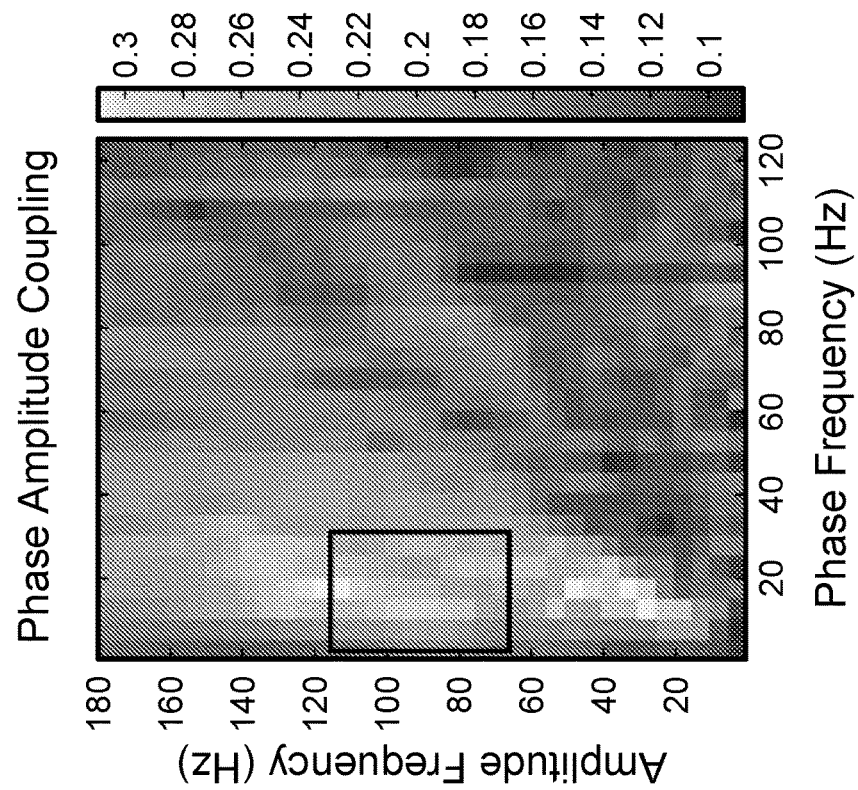
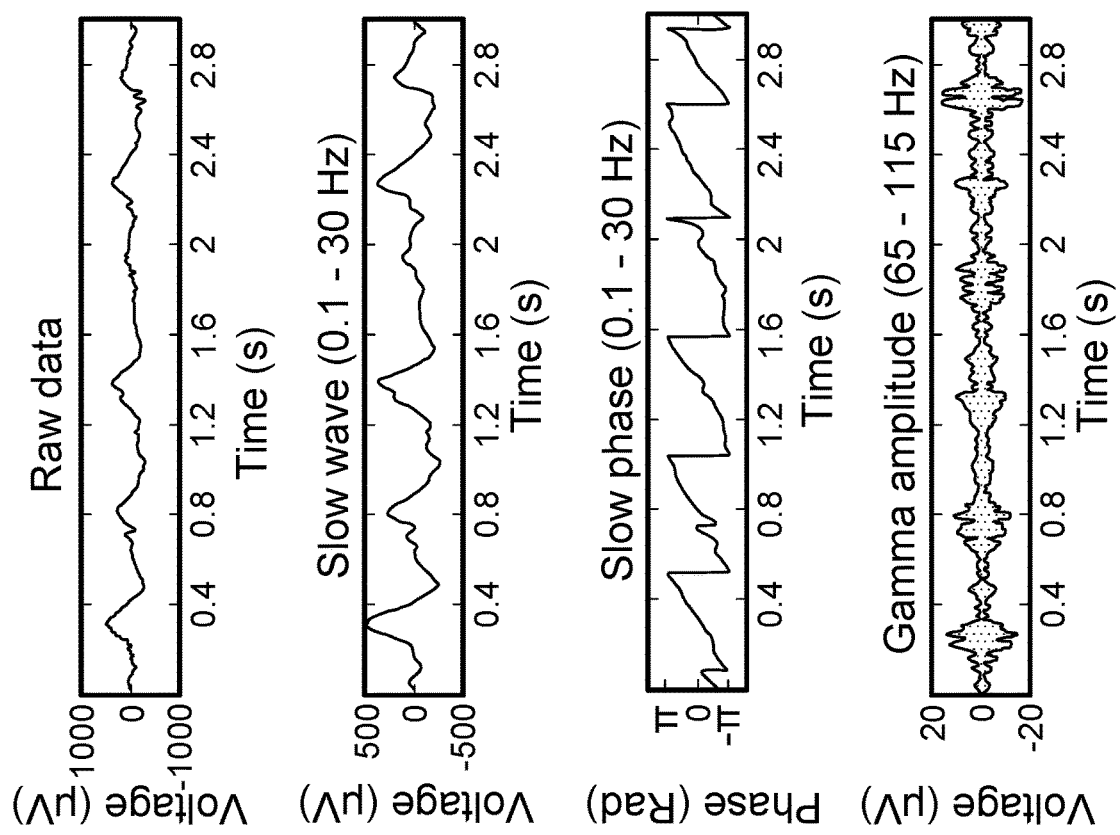
FIG. 8B
FIG. 8A

| Subject | SOZ | # channels | Electrode types | ILAE Score | AUC-PAC | AUC-PAC-BF | AUC-HFO | AUC-HFO-BF | AUC-IED | AUC-IED-BF |
|---|---|---|---|---|---|---|---|---|---|---|
| MSEL_00001 | RAT, LAT | 16 | Bilateral occipital approach depths | N/A | 1 | 0.75 | 0.875 | 0.875 | 0.6667 | 0.7083 |
| MSEL_00017 | LAT, RAT, amygdala | 62 | G, S, D | N/A | 0.8923 | 0.8615 | 0.7308 | 0.7317 | 0.4077 | 0.5423 |
| MSEL_00036 | RT, RO, RAT | 120 | G,S,D | 2 | 0.7546 | 0.7199 | 0.6753 | 0.6748 | 0.5768 | 0.5763 |
| MSEL_00038 | RAT, LAT | 15 | Bilateral occipital approach depths | N/A | 0.9167 | 0.8958 | 1 | 1 | 0.6042 | 0.7708 |
| MSEL_00055 | RAT, LAT | 15 | Bilateral occipital approach depths | N/A | 0.9375 | 0.9688 | 0.8281 | 0.8281 | 0.8516 | 0.8125 |
| MSEL_00069 | LMT | 78 | G,S,D | 2 | 0.8926 | 0.8564 | 0.5645 | 0.5508 | 0.877 | 0.8809 |
| MSEL_00078 | RAT, LF | 92 | G, S, D | 1 | 0.7532 | 0.862 | 0.4715 | 0.4778 | 0.6652 | 0.7297 |
| MSEL_00086 | LMT | 56 | G,D | N/A | 0.7411 | 0.8393 | 0.5982 | 0.6071 | 0.256 | 0.2649 |
| MSEL_00095 | RF, RP | 112 | G,S | N/A | 0.3914 | 0.4205 | 0.4508 | 0.4514 | 0.6313 | 0.6376 |
| MSEL_00109 | LAT | 56 | G,S,D | 5 | 0.7799 | 0.8459 | 0.6478 | 0.6541 | 0.4057 | 0.4182 |
| MSEL_00128 | RPT | 52 | G, S | 4 | 0.8299 | 0.7517 | 0.7891 | 0.7882 | 0.7856 | 0.8012 |
| MSEL_00139 | RP | 72 | G,S,D | N/A | 0.575 | 0.6318 | 0.5523 | 0.5523 | 0.6545 | 0.675 |
| MSEL_00147 | RF | 64 | G,D | N/A | 0.9592 | 1 | 0.699 | 0.7066 | 0.7398 | 0.8189 |
| MSEL_00150 | LMT | 63 | G,S,D | 4 | 0.9943 | 1 | 0.4783 | 0.4745 | 0.7726 | 0.8132 |
| MSEL_00157 | RF | 64 | G | 2 | 0.5387 | 0.7253 | 0.3844 | 0.3812 | 0.9242 | 0.9215 |
| MSEL_00175 | LF, LP | 68 | G, D | N/A | 0.9332 | 0.9478 | 0.6684 | 0.6669 | 0.6364 | 0.6705 |
| MSEL_00183 | LLT | 16 | Bilateral occipital approach depths | N/A | 1 | 1 | 1 | 1 | 0.9111 | 0.9111 |
| MSEL_00189 | LAT | 60 | G,S | 6 | 0.6444 | 0.65 | 0.646 | 0.646 | 0.8468 | 0.8421 |
| MSEL_00201 | RF | 92 | G,S,D | 1 | 0.7003 | 0.7761 | 0.7352 | 0.723 | 0.6594 | 0.6655 |
| MSEL_00209 | LMT, ILLT | 100 | G,S,D | 5 | 0.8807 | 0.8807 | 0.7733 | 0.7733 | 0.817 | 0.8591 |
| MSEL_00273 | RAT, RPT | 120 | G,S | 1 | 0.4082 | 0.2634 | 0.3616 | 0.3642 | 0.4464 | 0.456 |

FIG. 12A

| ID | Region | # | Type | | | | | | |
|---|---|---|---|---|---|---|---|---|---|---|
| MSEL_00288 | RAT | 45 | S,D | 0.9773 | 0.9773 | 0.9545 | 0.9545 | 1 | 1 |
| MSEL_00308 | LAT | 48 | G,S,D | 0.7948 | 0.7948 | 0.7649 | 0.7649 | 0.6494 | 0.6701 |
| MSEL_00327 | LAT, LF | 88 | G,S,D | 0.6701 | 0.7578 | 0.7058 | 0.7065 | 0.8734 | 0.8779 |
| MSEL_00333 | LF, LP | 76 | G | 0.6571 | 0.6232 | 0.7855 | 0.7836 | 0.528 | 0.5365 |
| MSEL_00338 | LAT | 64 | G,S,D | 0.9137 | 0.9137 | 0.8464 | 0.8477 | 0.7007 | 0.719 |
| MSEL_00344 | RAT | 104 | G,S,D | 0.9714 | 0.9561 | 0.9092 | 0.9092 | 0.648 | 0.699 |
| MSEL_00375 | LT Neocortex | 32 | G,S,D | 0.7266 | 0.7773 | 0.6211 | 0.6289 | 0.748 | 0.7598 |
| MSEL_00380 | LF, RF | 60 | G,S | 0.424 | 0.3603 | 0.6225 | 0.6262 | 0.7782 | 0.777 |
| MSEL_00384 | RF | 88 | G,S | 0.483 | 0.508 | 0.5207 | 0.5229 | 0.5037 | 0.5027 |
| MSEL_00397 | RAT, LAT | 16 | Bilateral occipital approach depths | 1 | 1 | 1 | 1 | 0.82 | 0.8 |
| MSEL_00402 | RF | 120 | G,S | 0.9121 | 0.9446 | 0.7293 | 0.7295 | 0.6988 | 0.6706 |
| MSEL_00406 | LAT | 15 | Bilateral occipital approach depths | 0.4167 | 0.5278 | 0.6806 | 0.6806 | 0.1667 | 0.3889 |
| MSEL_00415 | LAT | 56 | G,S,D | 0.7863 | 0.7453 | 0.6479 | 0.653 | 0.5795 | 0.6222 |
| MSEL_00416 | LF, LAT | 36 | G,S,D | 0.9423 | 0.9365 | 0.8077 | 0.8019 | 0.7904 | 0.8038 |
| MSEL_00417 | LP | 24 | G | 0.8444 | 0.8889 | 0.9389 | 0.9389 | 0.6556 | 0.6556 |
| MSEL_00418 | LF, LP | 24 | G | 0.6703 | 0.7143 | 0.5824 | 0.5989 | 0.989 | 0.9231 |
| MSEL_00419 | LAT | 50 | G,S,D | 1 | 1 | 0.9787 | 0.9787 | 0.7411 | 0.844 |
| MSEL_00420 | RF, RLT | 64 | G | 0.7087 | 0.6696 | 0.5529 | 0.5529 | 0.7899 | 0.7355 |
| MSEL_00440 | LMT | 35 | S,D | 0.7959 | 0.8673 | 0.3954 | 0.3954 | 0.75 | 0.7321 |
| MSEL_00442 | RAT, RF | 16 | Bilateral occipital approach depths | 1 | 1 | 0.4286 | 0.75 | 0.8571 | 0.9286 |
| MSEL_00447 | RAT | 84 | G,S,D | 0.8983 | 0.9075 | 0.9192 | 0.9192 | 0.7442 | 0.7383 |
| MSEL_00448 | LAT | 35 | S,D | 1 | 1 | 0.7672 | 0.7759 | 0.7989 | 0.7989 |
| MSEL_00449 | LAT | 24 | D | 0.7778 | 0.6667 | 0.5926 | 0.588 | 0.3981 | 0.412 |
| MSEL_00451 | RAT | 15 | Bilateral occipital approach depths | 0.4167 | 0.5833 | 0.6667 | 0.6667 | 0.75 | 0.6667 |

| | | | | | | | | | |
|---|---|---|---|---|---|---|---|---|---|
| MSEL_00452 | RT, LT | 16 | Bilateral occipital approach depths | N/A | 0.7455 | 0.7091 | 0.5273 | 0.5273 | 0.4909 | 0.5273 |
| MSEL_00453 | LAT | 16 | Bilateral occipital approach depths | 1 | 0.9286 | 0.9286 | 0.9286 | 0.9286 | 0.6429 | 0.6429 |
| MSEL_00454 | RAT | 44 | G,S | 3 | 0.9958 | 0.9895 | 0.9853 | 0.9853 | 0.9716 | 0.9737 |
| MSEL_00457 | RPF | 66 | G,S | 1 | 0.5219 | 0.4411 | 0.5219 | 0.5135 | 0.5 | 0.4899 |
| MSEL_00458 | RF | 84 | G,S,D | 5 | 0.7646 | 0.7017 | 0.5096 | 0.5126 | 0.6911 | 0.4914 |
| MSEL_00461 | LF | 120 | G,S | 1 | 0.9739 | 0.9435 | 0.9783 | 0.9783 | 0.513 | 0.4609 |
| MSEL_00475 | LF | 140 | G,S | 1 | 0.8246 | 0.8853 | 0.8583 | 0.8583 | 0.582 | 0.7524 |
| MSEL_00485 | LAT | 35 | G,D | 5 | 0.4398 | 0.5671 | 0.7407 | 0.7384 | 0.6944 | 0.6644 |
| MSEL_00491 | LF, LP, LT | 64 | G,S,D | N/A | 0.5973 | 0.6222 | 0.7632 | 0.7617 | 0.451 | 0.448 |
| MSEL_00494 | RF, RLT | 34 | G,S,D | 5 | 0.6845 | 0.7202 | 0.622 | 0.625 | 0.8214 | 0.8214 |
| MSEL_00497 | LAT | 56 | G,S,D | 3 | 0.383 | 0.4814 | 0.2394 | 0.2394 | 0.4202 | 0.4309 |
| MSEL_00501 | RP | 76 | G,S | 2 | 0.3862 | 0.5441 | 0.6036 | 0.5879 | 0.6263 | 0.6205 |
| MSEL_00511 | RF, RT | 80 | G,S | 3 | 0.6651 | 0.6112 | 0.6197 | 0.5609 | 0.5609 | 0.5632 |
| MSEL_00537 | LF, LT | 84 | G,S | 1 | 0.2272 | 0.3244 | 0.3244 | 0.3259 | 0.4945 | 0.5799 |
| MSEL_00538 | RT, RP, RF | 88 | G,S | 1 | 0.5522 | 0.4849 | 0.7006 | 0.6997 | 0.7429 | 0.7325 |
| MSEL_00540 | LAT, RAT | 15 | Bilateral occipital approach depths | N/A | 1 | 1 | 1 | 1 | 0.9333 | 0.85 |
| MSEL_00543 | RP | 80 | G,S | N/A | 0.693 | 0.6364 | 0.3494 | 0.3462 | 0.6838 | 0.6966 |
| MSEL_00548 | RT | 80 | G,S | 1 | 0.4935 | 0.7087 | 0.2635 | 0.2699 | 0.6187 | 0.5872 |
| MSEL_00552 | LAT | 76 | G,S,D | 3 | 0.8391 | 0.841 | 0.6494 | 0.6509 | 0.6193 | 0.6135 |
| MSEL_00555 | LPT | 70 | G,S,D | 4 | 0.6262 | 0.7031 | 0.5918 | 0.5891 | 0.6397 | 0.641 |
| MSEL_00557 | RF | 80 | G,S,D | 4 | 0.9622 | 0.9594 | 0.979 | 0.9832 | 0.8908 | 0.9027 |
| MSEL_00558 | LF | 128 | G,S,D | 5 | 0.4734 | 0.5053 | 0.6627 | 0.6669 | 0.6406 | 0.6381 |
| MSEL_00561 | RAT | 32 | G,S | 2 | 0.3875 | 0.3187 | 0.4438 | 0.4438 | 0.5297 | 0.5281 |
| MSEL_00564 | Unknown | 68 | G,S,D | N/A | 0.7823 | 0.6304 | 0.5096 | 0.5108 | 0.7883 | 0.7644 |

| | | | | | | | | | |
|---|---|---|---|---|---|---|---|---|---|
| MSEL_00565 | RF | 80 | G,S | 1 | 0.7292 | 0.8458 | 0.9729 | 0.975 | 0.5729 | 0.6896 |
| MSEL_00566 | RHemisphere | 28 | D | N/A | 0.5667 | 0.825 | 0.5111 | 0.525 | 0.5444 | 0.5417 |
| MSEL_00567 | LF | 104 | G,S | 1 | 0.6156 | 0.6181 | 0.444 | 0.4458 | 0.7757 | 0.7944 |
| MSEL_00569 | LF, LT, RT | 61 | G,S,D | 1 | 0.9901 | 0.9704 | 0.9298 | 0.9298 | 0.569 | 0.6342 |
| MSEL_00573 | RAT, RF | 88 | G,S,D | 1 | 0.8575 | 0.8687 | 0.8208 | 0.8204 | 0.6358 | 0.6313 |
| MSEL_00580 | RAT | 56 | G,S,D | 1 | 0.5551 | 0.4476 | 0.4313 | 0.4395 | 0.4401 | 0.4347 |
| MSEL_00605 | LT | 40 | G,S,D | 4 | 0.2545 | 0.7079 | 0.5197 | 0.5233 | 0.6022 | 0.6326 |
| MSEL_00607 | RT, RP, RT RAT | 124 | G,S | N/A | 0.5651 | 0.7529 | 0.824 | 0.8137 | 0.8706 | 0.849 |
| MSEL_00608 | LT, RT | 16 | D | 5 | 0.8182 | 0.8364 | 0.8182 | 0.8182 | 0.2909 | 0.2 |
| MSEL_00610 | LP, LF | 60 | G,S | 4 | 0.4461 | 0.4937 | 0.6253 | 0.6228 | 0.381 | 0.4612 |
| MSEL_00616 | RF | 90 | G,S | 1 | 0.8297 | 0.8141 | 0.6977 | 0.6953 | 0.8914 | 0.8781 |
| MSEL_00631 | LF, LP | 76 | G,S | 1 | 0.4245 | 0.4915 | 0.3919 | 0.39 | 0.5703 | 0.6087 |
| MSEL_00662 | | | | 1 | 0.9235 | 0.9088 | 0.8903 | 0.889 | 0.5424 | 0.5644 |
| Average | | | | | 0.7297 | 0.7513 | 0.6780 | 0.6824 | 0.6625 | 0.6754 |

FIG. 12D

| Subject | Best AUC (Table I) | PAC - entropy | | HFO - entropy | | IED - entropy | | Selected biomarker |
|---|---|---|---|---|---|---|---|---|
| | | Marginal | Conditional Reduction | Marginal | Conditional Reduction | Marginal | Conditional Reduction | |
| MSEL_00017 | PAC | 0.3546 | 0.3436 0.011 | 0.3876 | 0.3574 0.0302 | 0.6222 | 0.5966 0.0256 | HFO |
| MSEL_00038 | HFO | 0.5993 | 0.5965 0.0028 | 0.1461 | 0.1413 0.0048 | 0.7037 | 0.7036 0.0001 | HFO |
| MSEL_00150 | PAC | 0.5033 | 0.4948 0.0085 | 0.3893 | 0.3839 0.0054 | 0.8249 | 0.818 0.0069 | PAC |
| MSEL_00333 | HFO | 0.5627 | 0.5623 0.0004 | 0.0598 | 0.0584 0.0013 | 0.0598 | 0.0584 0.0013 | HFO |
| MSEL_00417 | HFO | 0.4601 | 0.4571 0.0031 | 0.3373 | 0.3371 0.0001 | 0.2805 | 0.2751 0.0053 | SPI |
| MSEL_00453 | PAC | 0.3896 | 0.3532 0.0364 | 0.4416 | 0.4379 0.0037 | 0.7282 | 0.7183 0.0099 | PAC |
| MSEL_00458 | PAC | 0.4138 | 0.4122 0.0016 | 0.4539 | 0.4398 0.0142 | 1.0752 | 1.0429 0.0323 | SPI |
| MSEL_00538 | SPI | 0.65 | 0.6437 0.0063 | 0.3373 | 0.3353 0.0019 | 0.3092 | 0.2997 0.0095 | SPI |
| MSEL_00607 | SPI | 0.5237 | 0.5233 0.0005 | 0.2175 | 0.2135 0.0041 | 0.277 | 0.2721 0.0049 | SPI |

FIG. 13

SEIZURE ONSET ZONE LOCALIZATION

CROSS-REFERENCE TO RELATED APPLICATIONS

This application is a National Stage application under 35 U.S.C. § 371 of International Application No. PCT/US2018/034703, having an International Filing Date of May 25, 2018, which claims priority to U.S. Application Ser. No. 62/511,239, filed on May 25, 2017. The disclosures of the prior applications are considered part of the disclosure of this application, and are incorporated in their entirety into this application.

STATEMENT AS TO FEDERALLY SPONSORED RESEARCH

This invention was made with government support under HL105355 awarded by National Institutes of Health. The government has certain rights in the invention.

BACKGROUND

One of the most burdensome and prevalent neurologic diseases is epilepsy. It is characterized by the occurrence of unprovoked seizures and affects ~1% of the population. Most epilepsy patients find relief with medication but a sizeable minority do not. In such cases options include among other things, surgical resection, but this option depends critically on accurate localization of the seizure onset zone (SOZ). Scalp electroencephalography (EEG) and Magnetic Resonance Imaging can at present only do so much to find the seizure onset zone. Gold standard localization involves the implantation of intracranial electrodes (iEEG) whereby electrodes are placed directly on the brain after part of the patient's skull has been removed; electrodes remain on or within brain for up to 30 days while the patient is in the ICU and waits for a sufficient number of seizures to occur. A trained epileptologist working with fellows and other neurologists and neurosurgeons determines the SOZ for a given patient based on a laborious and manual inspection of iEEG of multiple ictal events.

SUMMARY

This document describes systems, methods, devices, and other techniques for determining the location of a seizure-generating region of the brain of a mammal.

Some implementations of the subject matter disclosed herein include a computer-implemented method. The method can include obtaining, by a computing system, and for each of a plurality of sensor channels that each correspond to a respective electroencephalogram (EEG) sensor of a plurality of EEG sensors disposed at different locations of a brain of a mammal, a respective set of EEG data for the sensor channel that represents electrical activity during a first time interval at a particular location of the brain at which the EEG sensor that corresponds to the sensor channel is disposed; segmenting, by the computing system, and for each of the plurality of sensor channels, the respective set of EEG data for the sensor channel into a plurality of EEG data segments that each represent a respective portion of the set of EEG data for a different sub-interval of a plurality of sub-intervals that occur during the first time interval; for each sub-interval of the plurality of sub-intervals and for each sensor channel of the plurality of sensor channels: classifying, based at least on information derived from analyzing the EEG data segment that corresponds to the sub-interval and the sensor channel, the sensor channel as one of (i) a normal sensor channel having an EEG sensor that is likely not disposed at or near an epileptogenic region of the brain, or (ii) an abnormal sensor channel having an EEG sensor that is likely disposed at or near an epileptogenic region of the brain; and updating a value that represents a current cumulative belief that the sensor channel has an EEG sensor that is likely, or is likely not, disposed at or near an epileptogenic region of the brain; and providing, by the computing system, and for each of one or more of the plurality of sensor channels, an indication of whether the sensor channel has an EEG sensor that is likely, or is likely not, disposed at or near an epileptogenic region of the brain.

Some implementations of the subject matter disclosed herein include a method includes performing an electroencephalogram (EEG) procedure on a mammal, including obtaining intracranial EEG data during a first time interval for each a plurality of sensor channels, each sensor channel corresponding to a respective EEG sensor disposed at a location of a brain of the mammal that is different from the locations at which EEG sensors for other ones of the plurality of sensor channels are disposed; for each of the plurality of sensor channels, segmenting the intracranial EEG data for the sensor channel into a plurality of EEG data segments that each represent a respective portion of the intracranial EEG data for a different sub-interval of a plurality of sub-intervals that occur during the first time interval; applying a Bayesian filter to iteratively determine, for each sensor channel of the plurality of sensor channels, a classification of the sensor channel as one of (i) a normal sensor channel having an EEG sensor that is likely not disposed at or near an epileptogenic region of the brain, or (ii) an abnormal sensor channel having an EEG sensor that is likely disposed at or near an epileptogenic region of the brain; using the classifications of the plurality of sensor channels, locating a first epileptogenic region of the brain; and resecting the first epileptogenic region of the brain.

DESCRIPTION OF DRAWINGS

FIGS. 8A-8D depicts plots of phase amplitude coupling (PAC), high frequency oscillations (HFO) and interictal epileptiform discharge (IED) detection. FIG. 8A is a detailed illustration of the PAC feature extraction algorithm. Slow (0.1-30 Hz) and high (65-115 Hz) frequency components are filtered out from the raw signal. Phase of the slow wave is correlated with the high frequency amplitude envelope to measure coupling. FIG. 8B is a PAC-gram representing the average interictal PAC measured between different frequency bands. Highlighted portion indicates the low and high frequency bands utilized in rest of our analysis. FIG. 8C is a pictorial illustration of HFO detection. Oscillations that have an amplitude of three standard deviations above the mean and lasting for more than one complete cycle in low gamma (30-60 Hz), high gamma (60-100 Hz) and ripple (100-150 Hz) bands are detected. FIG. 8D is an illustration of detected IEDs. Differential amplitude is standardized and a threshold of four standard deviations around the mean was used to mark IEDs.

FIG. 9A shows a flow diagram depicting the different components of the algorithm. A 2-hour data segment is divided into 3-second epochs. PAC, HFO and IED features are extracted in these epochs and a clustering method is used to classify abnormalities (shown in FIG. 9B). Binary observations are assigned based on biomarker abnormalities and a likelihood for a channel being in the SOZ is tracked using a Bayesian filter. FIG. 9B shows classified abnormalities based on PAC features and the evolution of the respective likelihood probabilities are shown in FIG. 9C. These likelihood probabilities are then compared against the gold standard SOZs to generate ROC curve (shown in FIG. 9D). A box plot showing the distribution of the likelihood probabilities assigned by the algorithm for channels in SOZ and non SOZ regions is shown in FIG. 9E. FIG. 9F shows detected SOZ, detected non SOZ, gold standard SOZ and bad electrodes are shown in a 3D model brain. The mean of all the likelihood probabilities was used as the threshold to classify SOZ and non SOZ electrodes.

FIGS. 10A-10O depicts plots that show how a Bayesian filter can provide improvements in AUC for different biomarkers, the AUCs obtained using different biomarkers showing significant correlation and disagreements with gold standard SOZ correlates with bad surgical outcomes. FIG. 10A shows a comparison between the overall AUCs obtained for each biomarker evaluated with and without Bayesian filter (BF indicates Bayesian filter was used). Overall, PAC provided the best AUCs regardless of the usage of Bayesian filter. Using Bayesian filter, small improvements were achieved with PAC (p=0.04) and IED (p=0.04) while the improvement was not significant with HFO (p=0.27).

FIG. 11A shows 72-second recording of 6 channels, at the beginning of the analysis segment was selected. FIG. 11B shows signal abnormalities were manually annotated. PAC (FIG. 11C), HFO (FIG. 11D), and IED (FIG. 11E) features were extracted for this duration. Marginal and conditional entropies were calculated for all the features based on the annotations. A large reduction in entropy when conditioned on the annotations means that the biomarker is significantly correlated with the annotations. In that regard, for the particular test subject, IEDs best explain the annotations and is pre-selected by the algorithm. FIG. 11F plots entropy.

FIGS. 12A-12D is a table depicting patient information and results from the study of example 1. For each patient, clinical SOZ, number and type(s) of electrodes implanted, surgical outcome and AUCs obtained using the described SOZ detection algorithm for PAC, PAC with Bayesian filter, HFO, HFO with Bayesian filter, IED and IED with Bayesian filter are reported. G, S, and D denote grid, strip and depth electrode types. ILAE outcomes range between 1-6 and N/A represents situations when no respective surgery was performed. AUC values highlighted in red denote when using the Bayesian filter improved the localization AUC. FIG. 12A shows a first portion of the table, FIG. 12B shows a second portion of the table, FIG. 12C shows a third portion of the table, and FIG. 12D shows a fourth portion of the table.

FIG. 13 is a table depicting the results of the devised biomarker pre-selection technique on a chosen nine patients. A short recording at the beginning of the analysis segment was selected for nine patients. Signal abnormalities were manually annotated and PAC, HFO and IED features were extracted for this duration. Marginal and conditional entropies were calculated for all the features based on the annotations. A large reduction in entropy when conditioned on the annotations means that the biomarker is significantly correlated with the annotations. For each patient analyzed, the biomarker that provided the best AUC (per table in FIGS. 12A-D), marginal, conditional and reduction in entropy for PAC, HFO and IED and the selected biomarker based on the largest reduction in entropy are listed in this table. Highlighted in red are the maximum reductions in entropy obtained for each patient as well as when the preselected biomarker and the biomarker resulted with best AUC in table from FIGS. 12A-D match.

Like reference symbols in the various drawings indicate like elements.

DETAILED DESCRIPTION

Figure 1:
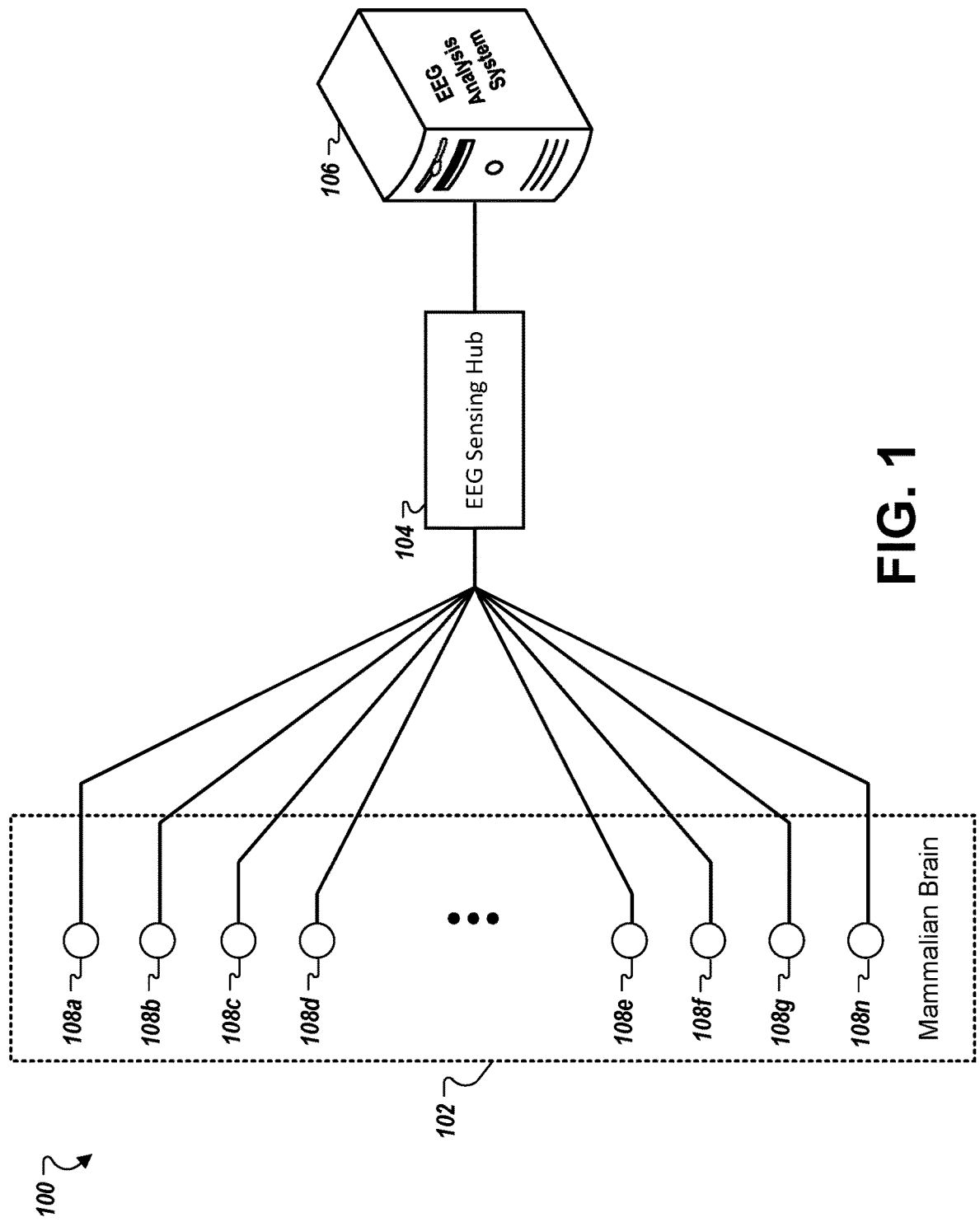
FIG. 1 shows an example environment in which intracranial EEG ("iEEG") data is collected and analyzed to determine the locations of one or more seizure generating regions of a brain of a mammal.

This document describes systems, methods, devices, and other techniques for determining the location of a seizure-generating region of the brain of a mammal. The seizure-generating region is alternately referred to herein as an epileptogenic region or a seizure-onset zone ("SOZ"). Surgical removal of seizure-generating brain tissue (i.e., resection) can cure epilepsy in patients who do not respond to medications. However, identifying seizure-generating regions has proven difficult and unreliable in many instances, particularly since conventional techniques have relied on analysis of ictal electroencephalogram ("EEG") recordings to localize the seizure-onset zone. Ictal EEG recordings refer to signals recorded in patients during a seizure, which can be expensive and time-consuming to obtain, since patients are often connected to intracranial EEG sensors and must wait until one or more seizures occur to obtain the requisite data that can be analyzed to estimate the location of the seizure-generating region of the brain.

This paper discusses techniques that, in some implementations, may at least partially address these shortcomings by allowing for localization of the seizure-onset zone using inter-ictal EEG data, which is recorded between epileptic events (e.g., seizures), rather than during such events. In this way, patient monitoring may commence shortly after implantation of the intracranial EEG electrodes, without needing to wait extended periods for the occurrence of seizure(s) for collection of ictal EEG data. Moreover, some implementations of the techniques disclosed herein identify in EEG data transient events that can be indicative of a seizure-generating region of the brain using temporal or frequency-based spectral analysis techniques to determine values of features that are clinically effective but less computationally expensive than other techniques. Thus, the techniques herein may be used to carry out localization of epileptogenic brain region using only inter-ictal EEG data, rather than as a complement to localization techniques based on ictal EEG data.

In general, the techniques disclosed herein include unsupervised and automatic inter-ictal SOZ localization, which leverage two empirical observations made from data relating to the temporal disposition of abnormal events (also referred to as transient events, these events are inter-ictal events that tend to occur in the electrical activity of epileptogenic brain regions to a greater degree than non-epileptogenic regions). First, the techniques leverage the repetitive (or deterministic) nature of the abnormal events that are observed in SOZ channels. That is, a sensor channel which previously exhibited an abnormal event has a high likelihood of exhibiting such events in the future. Accordingly, the techniques disclosed herein can use a Bayesian filter to segregate the sensor channels that show a significant degree of determinism in exhibiting abnormal events from sensor channels that do not exhibit such degree of determinism. Second, the techniques herein build upon the observation that, apart from the rate (e.g., events/minute) of the abnormal events, their temporally synchronized occurrence across adjacent channels is also a differentiator. Some disclosed implementations use a grouping strategy based, e.g., on K-means clustering, to group channels based on the temporal similarity of abnormal events.

Referring now to FIG. 1, an example environment 100 is shown in which intracranial EEG ("iEEG") data is collected and analyzed to determine the locations of one or more seizure generating regions of a brain 102 of a mammal (e.g., a human). A set of EEG electrodes 108a-n are placed at various locations within the brain 102. Each EEG electrode 108 is configured to monitor the electrical activity of the brain 102 in a region at or near the electrode 108 and to transmitting a wired or wireless signal that is representative of the detected electrical activity to the EEG sensing hub 104. The number of electrodes 108 disposed within the brain 102 may vary, but may for example be in the range of 14 to 512 electrodes. In some implementations, absolute locations of the electrodes 108 in the brain 102 are mapped and/or the locations of the electrodes 108 relative to each other are mapped to allow determination of the approximate boundaries of an epileptogenic region based on which sensors are determined to be located at or near the epileptogenic region.

The EEG sensing hub 104 receives signals from each of the electrodes 108a-n. The respective signal received from each of the sensors 108a-n corresponds to a unique sensor channel. The hub 104 may process signals over many sensor channels at once to allow for parallel collection, recording, and processing of EEG sensor data. In some implementations, the hub 104 performs one or more pre-processing operations before EEG data for each of the sensor channels is provided to the EEG analysis computing system 106. For example, the hub 104 may amplify and filter the raw signals detected by electrodes 108a-n. The hub 104 may digitize the signals and normalize them as well. The hub 104 can also generate EEG data segments by splitting a continuous stream of EEG data into small chunks that each corresponds to EEG data collected over a short time interval (e.g., between 2-5 seconds, and preferably about 3 seconds). In some implementations, the EEG sensing hub 104 is physically and/or logically separate from the EEG analysis computing system 106. In other implementations, the hub 104 is physically and/or logically part of the computing system 106.

The EEG analysis computing system 106 may be implemented as one or more computers in one or more locations. In general, the system 106 can be configured to process EEG data (e.g., iEEG data obtained based on signals from electrodes 108a-n) to determine which sensor channels correspond to electrodes that are likely located at or near an epileptogenic brain region, and which sensor channels are not. For simplicity, this document sometimes refers to sensor channels having sensors that are located away from an epileptogenic region as 'normal' channels, and sensor channels having sensors that are located at or near an epileptogenic region as 'abnormal' channels. Sometimes the classification of a sensor channel as normal or abnormal takes made based on analysis of an EEG data segment within a particular epoch (sub-interval of time), but the classification of the channel for that epoch is an intermediate or non-final classification made according to the observation of data for that epoch (e.g., whether the data segment for the epoch contains an abnormal/transient event associated with a seizure-generating region). A cumulative belief may be iteratively updated by processing EEG data segments across a series of many epochs to determine a final estimated classification of each channel's status as a normal or abnormal channel that likely does not, or likely does, respectively, have an electrode disposed within an epileptogenic region of the brain. Further detail concerning the EEG analysis computing system 106 is discussed with respect to FIG. 3.

Figure 2:
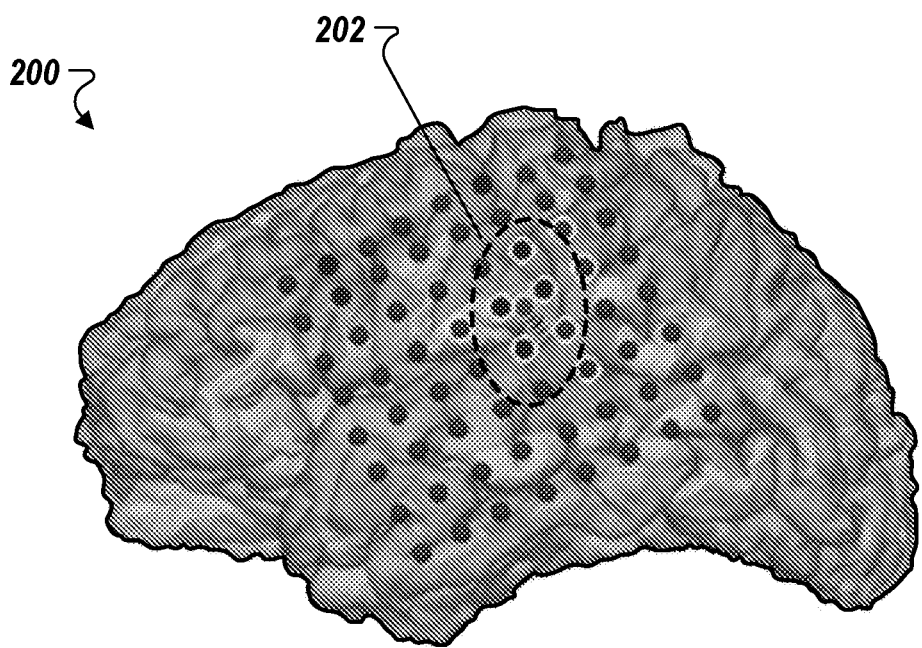
FIG. 2 depicts an example diagram of a brain having a set of electrodes placed therein.

FIG. 2 depicts an example diagram of a brain 200 having a set of electrodes, e.g., electrodes 108a-n, placed therein. The electrodes are disposed at different locations of the brain 200 so as to enable the identification of seizure-generating region. For example, the electrodes within region 202 (indicated by the dashed oval) may be classified as abnormal by an EEG analysis computing system based, for example, on the identification of frequent abnormal inter-ictal events at local regions near these electrodes. The electrodes located outside of the boundary of region 202 are classified as normal and thus correspond to non-seizure onset zones of the brain 200.

Figure 3:
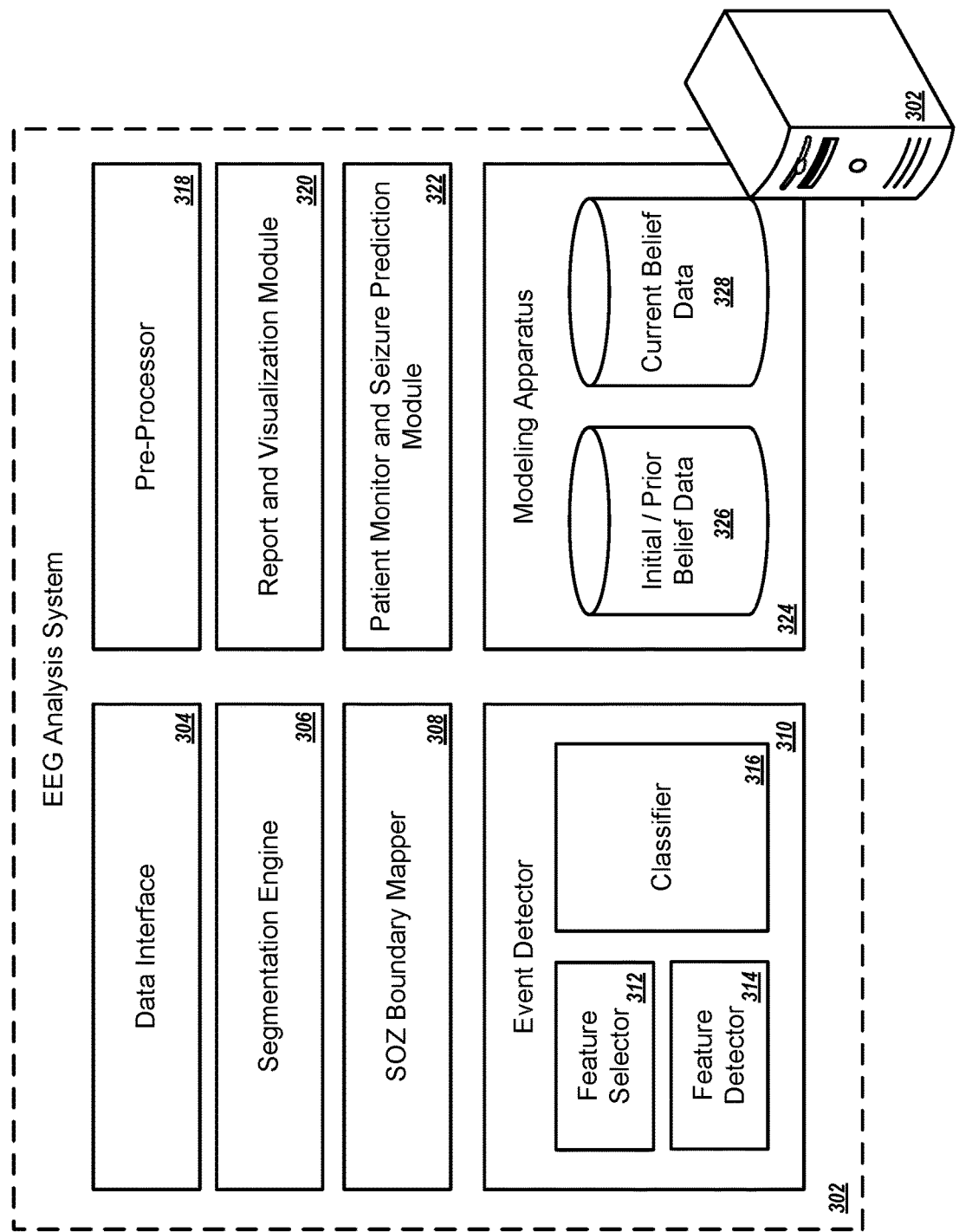
FIG. 3 is a block diagram of an example EEG analysis computing system.

FIG. 3 is a block diagram of an example EEG analysis computing system 302. The system 302 may be implemented as one or more computers in one or more locations. In some implementations, the system 302 is configured in a like manner to system 106 from FIG. 1. The system 302 can include one or more of a data interface 304, a pre-processor 318, a segmentation engine 306, an event detector 310, a modeling apparatus 324, a report and visualization module 320, an SOZ boundary mapper 308, and a patient monitor and seizure prediction module 322. Each of the components may implemented, for example, based on a combination of computer hardware and software.

The data interface 304 is configured to receive baseline EEG data (e.g., iEEG data) from an external sensing hub (e.g. hub 104) or from EEG electrodes directly. The preprocessor 318 processes the baseline EEG data to generate pre-processed EEG data that is suitable for further processing by other components of the system 302. The segmentation engine 306 divides the respective stream of EEG data for each sensor channel into a segments of EEG data, where each segment for a given channel includes EEG data for a particular epoch (sub-interval) of the stream. The segmentation engine 306 can generate an EEG data matrix such as the matrix 400 depicted in FIG. 4. In some implementations, the EEG data is split into segments of fixed sub-intervals of time such as 1, 2, 3, 4, or 5 seconds.

The event detector 310 is configured to process segments of EEG data for one or more channels within a given epoch and to classify the respective sensor channels that correspond to the processed data segments as normal or abnormal. The classification can be based, for example, on whether an abnormal event is detected in a data segment that is associated with epileptic activity. A feature selector 312 configures the event detector 310 to classify sensor channels based on values of one or more features specified by the selector 312. The features may be selected based on user input received to the feature selector 312 that indicates which features should be applied in a given circumstance. Different features may be selected, for example, based on characteristics of the patient, based on the quantity of available data, based on validation of the reliability of different features over time, or a combination of these. For instance, the feature selector 312 may select among power-in-band, high-frequency oscillations, inter-ictal spikes, phase amplitude coupling, ora combination of these and other features. The feature detector 314 analyzes the EEG data segment for a given channel to determine values for one or more features of the portion of the EEG represented by the data segment. The values are determined for the features indicated by the feature selector 312.

Power-in-band features can be extracted as wavelet, Hilbert, or short-time Fourier transform (SIFT) spectral powers in the frequency bands Delta (0-3 Hz), Low-Theta (3-6 Hz), High-Theta (6-9 Hz), Alpha (9-14 Hz), Beta (14-25 Hz), Low-Gamma (30-55 Hz), High-Gamma (65-115 Hz), and Ripple (>125 Hz). Inter-ictal spikes can be characterized as brief (e.g., <250 millisecond) morphologically defined events observed in the EEGs of patients predisposed to spontaneous seizures of focal onset. The spikes are generated by the synchronous discharges of a group of neurons in a region referred to as the epileptic focus. Phase-amplitude coupling represents the higher amplitude, low frequency oscillations of the brain which are believed to modulate long-distance communication between different areas in the brain by regulating the excitability of smaller scale ensembles. The phase of these slow waves can affect the HFO. PAC facilitates effective interactions between neurons that have a similar phase preference, synchronizing firing of neurons at high frequencies. HFO is as an electrophysiologically detectable oscillation with a central frequency between, e.g., 30-600 Hz. The high frequency oscillations (HFOs) are essentially all those above 30 Hz. They are transient, possessing multiple 'turns' sinusoidal in nature. These events can occur on the order of a few dozen milliseconds and occur spontaneously in the hippocampus, during slow wave sleep primarily, and can also be seen in the neocortex.

Generally, the same features are selected to evaluate all EEG data segments for a patient across all the channels and epochs, but different features may be selected in different sessions (e.g., for different patients). The classifier 316 processes the determined values of the features to classify channels as normal or abnormal based on whether the corresponding EEG data segments for the channels are determined to exhibit an abnormal event, as indicated by the values of the one or more features for the data segments. In some implementations, a sensor channel is classified as normal or abnormal based on whether its corresponding EEG segment has a feature value that satisfies a threshold value. In some implementations, a sensor channel is classified as normal or abnormal based on an unsupervised clustering technique that groups channels using, e.g., K-means clustering, according to the determined feature values for the EEG data segments of the corresponding channel.

For each epoch in a series of epochs, the event detector 310 determines a classification for each sensor channel. At each epoch, the modeling apparatus 324 then obtains the classifications for the sensor channels at the epoch and updates current belief data 328 based on these classifications. The current belief data 328 is iteratively updated after each epoch and represents a cumulative belief as to the statuses (normal or abnormal) of each channel based on an initial belief and the classifications at each previous epoch through the current epoch The modeling apparatus 324 maintains a data repository 326 that indicates the belief of each channel's status at a preceding epoch and maintains a data repository 328 that indicates the belief of each channel's status at the current epoch. In some implementations, beliefs are indicated by a numerical score that represents a probability (or other likelihood) that a sensor channel is a normal or abnormal channel. After the data segments for the final epoch within an analysis window has been processed, the current belief data can indicate final likelihoods of each sensor channel having an electrode disposed at or near an epileptogenic brain region. In some implementations, the modeling apparatus 324 implements a Bayesian filter to iteratively update the current belief data at each time epoch.

In some implementations, the system 302 includes a report and visualization module 320. The module 320 can generate reports indicating, for example, the final classification of each sensor channel as normal or abnormal, and/or the numerical scores indicating the likelihood of each channel being normal or abnormal. The system 302 can further include an SOZ boundary mapper 308. The boundary mapper 308 identifies data indicating the spatial location of each EEG electrode in the brain, and obtains final classifications for each sensor channel from the modeling apparatus 324. The mapper 308 then correlates these data to determine the physical locations and/or boundaries of a seizure-generating region of the brain. For example, the seizure-generating region may span the smaller detection regions associated with a group of adjacent intra-cranial electrodes corresponding to sensor channels that were finally classified as abnormal. In some implementations, a diagram of the brain and the detection region (e.g., a 2D or 3D diagram) may be generated and displayed to the user or included in a report from the module 320.

The system 302 can also include a patient monitor and seizure prediction module 322. Whereas the event detector 310 and modeling apparatus 324 are configured to process inter-ictal EEG data to determine the location of epileptogenic region of a brain, the module 322 is configured to analyze inter-ictal EEG data to predict when an epileptic event (e.g., a seizure) will occur. In some implementations, the modeling apparatus 324 can provide to the module 322 an indication of which sensor channels are classified as abnormal. The module 322 can use the classifications to affect a manner in which the seizure predictions are made. For example, the module 322 may select to monitor and analyze only EEG data received over the abnormal channels when making predictions. Alternatively, the weight assigned to events detected in abnormal channels may be skewed relative to the weight assigned to events detected in normal channels when making predictions that an epileptic event will occur.

Figure 4:
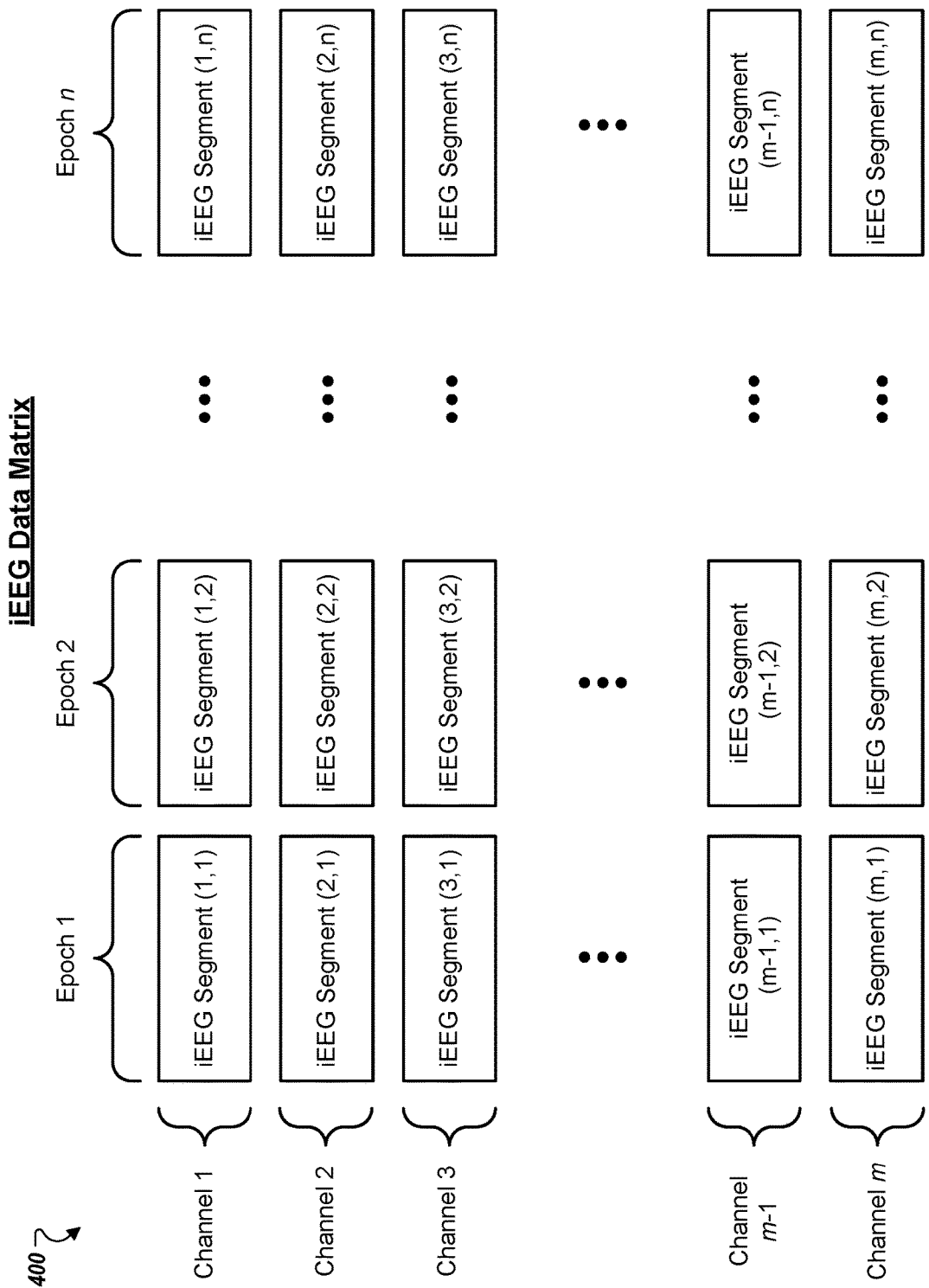
FIG. 4 shows an example matrix having a set of iEEG data segments.

FIG. 4 shows an example iEEG data matrix 400. The matrix 400 includes a set of iEEG data segments. The matrix 400 can be generated by a segmentation engine, e.g., segmentation engine 306. The matrix 400 has m rows and n columns. Each row provides segments of EEG data from a different sensor channel. Each column provides segments of EEG data from a different epoch. For example, the first epoch (column 1) may represent the first three seconds of recorded iEEG data during an analysis interval, the second epoch (column 2) may represent the next three seconds of recorded iEEG data during the analysis interval, and so on. Each segment can be represented by a coordinate that identifies its position in the matrix 400 by row and column.

Figure 5:
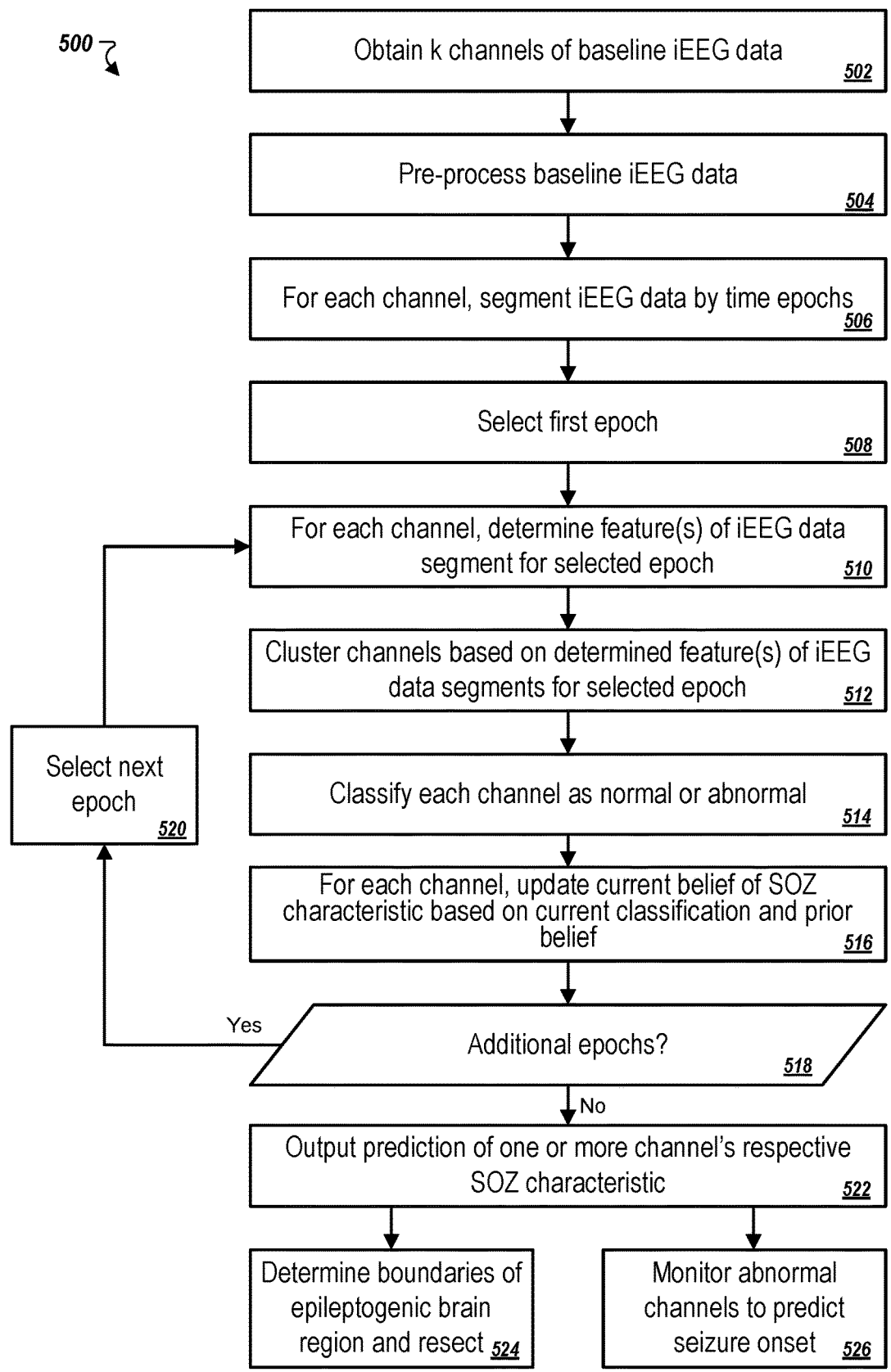
FIG. 5 depicts a flowchart of an example process for identifying the location of a seizure-generating region of a brain of a mammal.

FIG. 5 depicts a flowchart of an example process 500 for identifying the location of a seizure-generating region of a brain of a mammal. In some implementations, the process 500 is performed by an EEG analysis computing system, such as systems 106 or 302 (although resection in stage 524, and certain other steps may be performed by a human).

At stage 502, the system obtains k channels of baseline iEEG data. The baseline iEEG data may represent electrical activity of the brain recorded over a first time interval. The first time interval may be, in the range of 15 minutes to 8 hours, for example, and is preferably in the range of 1.5 hours to 3 hours, e.g., 2 hours. Each channel carries iEEG data from a corresponding electrode disposed at the brain of a subject. At stage 504, the system pre-processes the baseline iEEG data, and at stage 506, the system temporally divides the data for each channel into a set of iEEG data segments. A data segment can be generated for each channel at each sub-interval (epoch) of the first time interval.

The process 500 may iteratively update a current belief as to the status (e.g., normal or abnormal) of each of the sensor channels. A first iteration begins at stage 508, where the data segments of the sensor channels for an initial epoch is selected. At stage 510, the system analyzes the respective data segment for each channel at the initial epoch to determine values for one or more features of the data segment. At stage 512, the system then clusters the sensor channels by generating groups of channels based on similarities of the feature values for the corresponding data segments at the selected epoch. A first cluster (or set of clusters) of sensor channels can be designated as abnormal sensor channels based on one or more criteria. The remaining clusters can be designated as normal sensor channels. These classifications form an observation each of the sensor channels at the current epoch, which is used to update the current belief of the true classifications of the channels (stage 516). In some implementations, the system implements a Bayesian filter to update the current belief of the true classification of each channel based on a prior belief for the channel and the observation of the classification at the current time step.

At stage 518, the system checks whether the end of the first time interval has been reached or if data segments for additional epochs remain to be processed. If additional epochs remain, the system selects the data segments for the next epoch at stage 520, and continues processing from stage 510. Once the data segments for the final epoch have been processed, the system proceeds to stage 522 and outputs an indication of the final belief of the true classification of one or more of the sensor channels. For example, the system may generate a report that identifies which sensor channels are determined to likely correspond to EEG sensors disposed at or near an epileptogenic brain region (i.e., the abnormal sensor channels). In some implementations, the system may provide for display on an electronic display device a 2D or 3D model of the brain showing the locations of monitored electrodes, which electrodes are classified as normal or abnormal, and/or the boundaries of the determined epileptogenic brain region. The output can be applied to various ends. For example, at stage 524, a surgeon may use the indication of the location of the epileptogenic region to perform a surgery to resect this region of the brain from a patient. In some implementations, at stage 526, the system monitors abnormal channels to predict seizure onset, e.g., with a patient monitor and seizure prediction module 322.

Figure 6:
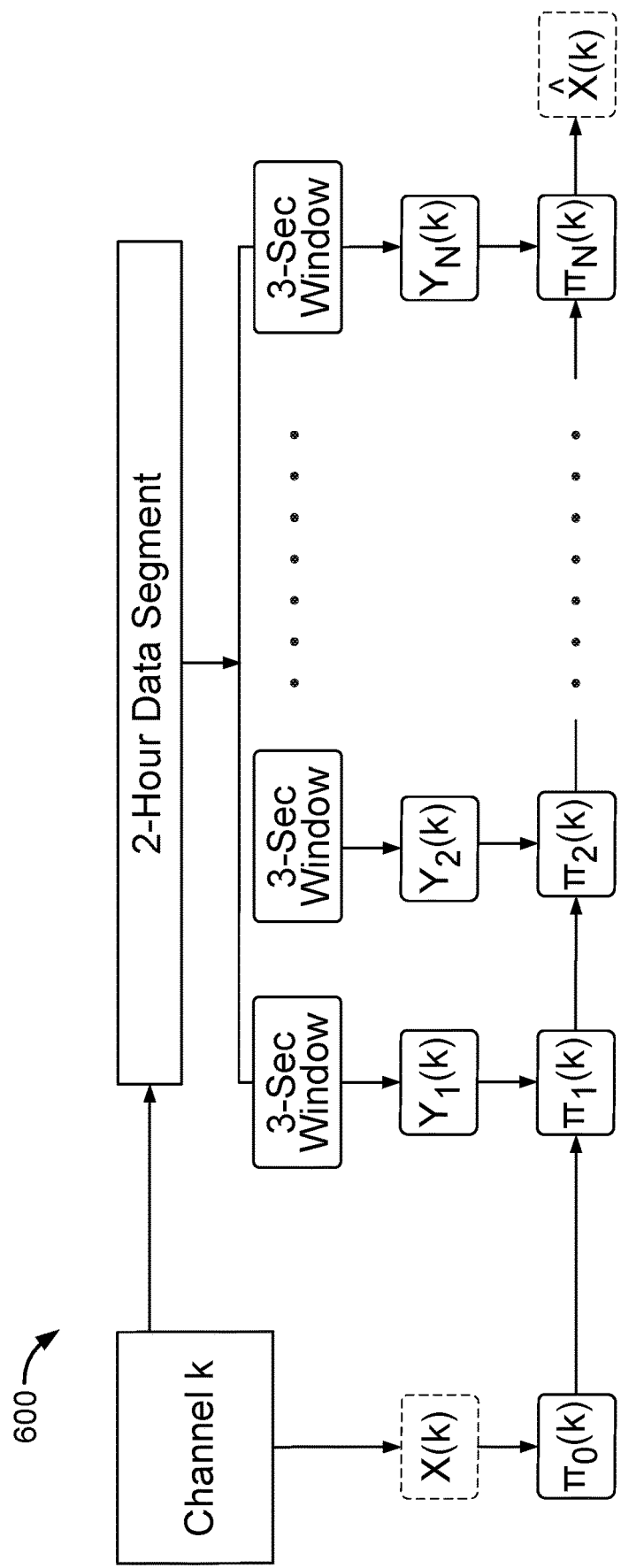
FIG. 6 shows a flow diagram of an example process for using a Bayesian filter to estimate the true status of a channel k of iEEG data, i.e., whether the channel corresponds to a sensor located at or near an epileptogenic region of the brain (an abnormal channel) or whether the channel corresponds to a sensor located away from an epileptogenic region of the brain.

FIG. 6 shows a flow diagram of an example process 600 for using a Bayesian filter to estimate the true status of a channel k of iEEG data, i.e., whether the channel corresponds to a sensor located at or near an epileptogenic region of the brain (an abnormal channel) or whether the channel corresponds to a sensor located away from an epileptogenic region of the brain. The channel's true state (whether channel k is in SOZ or not) is denoted by X(k), and the initial belief about (k) is denoted by $\pi_0(k)$. The observation $Y_n(k)$ at an epoch n is used to iteratively update $\pi_n(k)$. The current belief after N epochs, $\pi_N(k)$, is used to estimate the true state. The estimate true state is represented by X(k).

Figure 7:
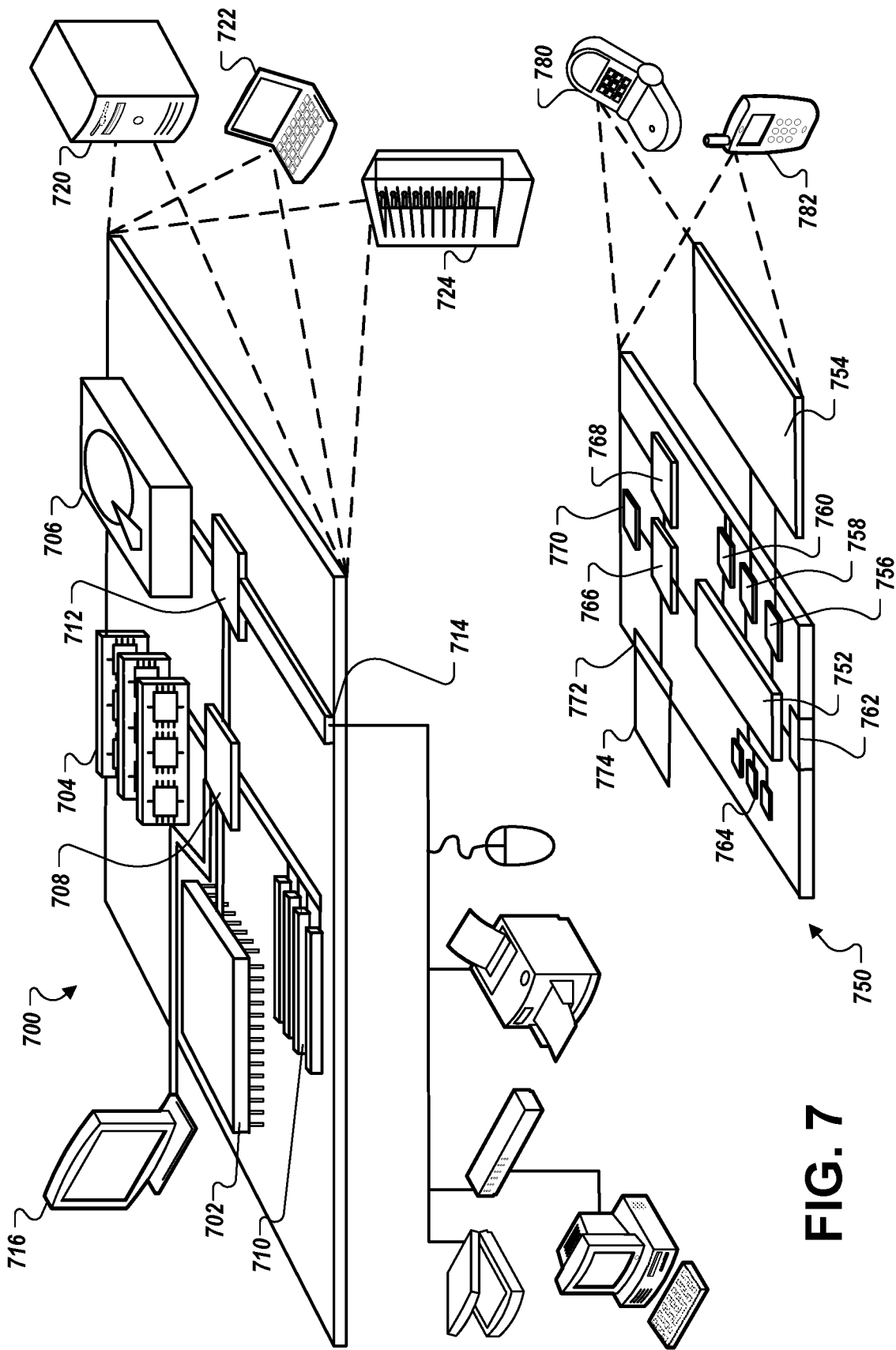
FIG. 7 shows an example of a computing device and a mobile computing device that can be used to implement the techniques described herein.

FIG. 7 shows an example of a computing device 700 and a mobile computing device that can be used to implement the techniques described herein. The computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 may also be another form of computer-readable medium, such as a magnetic or optical disk.

The storage device 706 is capable of providing mass storage for the computing device 700. In some implementations, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. The computer program product may also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. In some implementations, the high-speed interface 708 is coupled to the memory 704, the display 716 (e.g., through a graphics processor or accelerator), and to the high-speed expansion ports 710, which may accept various expansion cards (not shown). In the implementation, the low-speed interface 712 is coupled to the storage device 706 and the low-speed expansion port 714. The low-speed expansion port 714, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. In addition, it may be implemented in a personal computer such as a laptop computer 722. It may also be implemented as part of a rack server system 724. Alternatively, components from the computing device 700 may be combined with other components in a mobile device (not shown), such as a mobile computing device 750. Each of such devices may contain one or more of the computing device 700 and the mobile computing device 750, and an entire system may be made up of multiple computing devices communicating with each other.

The mobile computing device 750 includes a processor 752, a memory 764, an input/output device such as a display 754, a communication interface 766, and a transceiver 768, among other components. The mobile computing device 750 may also be provided with a storage device, such as a micro-drive or other device, to provide additional storage. Each of the processor 752, the memory 764, the display 754, the communication interface 766, and the transceiver 768, are interconnected using various buses, and several of the components may be mounted on a common motherboard or in other manners as appropriate.

The processor 752 can execute instructions within the mobile computing device 750, including instructions stored in the memory 764. The processor 752 may be implemented as a chipset of chips that include separate and multiple analog and digital processors. The processor 752 may provide, for example, for coordination of the other components of the mobile computing device 750, such as control of user interfaces, applications run by the mobile computing device 750, and wireless communication by the mobile computing device 750.

The processor 752 may communicate with a user through a control interface 758 and a display interface 756 coupled to the display 754. The display 754 may be, for example, a TFT (Thin-Film-Transistor Liquid Crystal Display) display or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may provide communication with the processor 752, so as to enable near area communication of the mobile computing device 750 with other devices. The external interface 762 may provide, for example, for wired communication in some implementations, or for wireless communication in other implementations, and multiple interfaces may also be used.

The memory 764 stores information within the mobile computing device 750. The memory 764 can be implemented as one or more of a computer-readable medium or media, a volatile memory unit or units, or a non-volatile memory unit or units. An expansion memory 774 may also be provided and connected to the mobile computing device 750 through an expansion interface 772, which may include, for example, a SIMM (Single In Line Memory Module) card interface. The expansion memory 774 may provide extra storage space for the mobile computing device 750, or may also store applications or other information for the mobile computing device 750. Specifically, the expansion memory 774 may include instructions to carry out or supplement the processes described above, and may include secure information also. Thus, for example, the expansion memory 774 may be provide as a security module for the mobile computing device 750, and may be programmed with instructions that permit secure use of the mobile computing device 750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. The computer program product contains instructions that, when executed, perform one or more methods, such as those described above. The computer program product can be a computer- or machine-readable medium, such as the memory 764, the expansion memory 774, or memory on the processor 752. In some implementations, the computer program product can be received in a propagated signal, for example, over the transceiver 768 or the external interface 762.

The mobile computing device 750 may communicate wirelessly through the communication interface 766, which may include digital signal processing circuitry where necessary. The communication interface 766 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 768 using a radio-frequency. In addition, short-range communication may occur, such as using a Bluetooth, WiFi, or other such transceiver (not shown). In addition, a GPS (Global Positioning System) receiver module 770 may provide additional navigation- and location-related wireless data to the mobile computing device 750, which may be used as appropriate by applications running on the mobile computing device 750.

The mobile computing device 750 may also communicate audibly using an audio codec 760, which may receive spoken information from a user and convert it to usable digital information. The audio codec 760 may likewise generate audible sound for a user, such as through a speaker, e.g., in a handset of the mobile computing device 750. Such sound may include sound from voice telephone calls, may include recorded sound (e.g., voice messages, music files, etc.) and may also include sound generated by applications operating on the mobile computing device 750.

The mobile computing device 750 may be implemented in a number of different forms, as shown in the figure. For example, it may be implemented as a cellular telephone 780. It may also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In situations in which the systems, methods, devices, and other techniques here collect personal information (e.g., context data) about users, or may make use of personal information, the users may be provided with an opportunity to control whether programs or features collect user information (e.g., information about a user's social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

Example Implementation 1

This example delineates a study of a semi-supervised technique that attempts at subject-specific (e.g., patient-specific) feature selection and demonstrates its efficacy on a set of chosen patients. Apart from these, results of the study indicate that utilizing a Bayesian filter and temporal grouping strategy on top of a selected feature, on average, improves the localization of SOZ (epileptogenic brain region) accuracy regardless of the biomarker (e.g., feature) used.

Experimental Setup.

All subjects provided informed consent. Subjects underwent intracranial depth electrode implantation as part of their evaluation for epilepsy surgery when non-invasive studies could not adequately localize the origin of seizure generation (SOZ).

Subjects.

Data from eighty-two subjects with focal and multifocal epilepsy were investigated by post hoc analysis. All subjects were implanted with intracranial depth arrays, grids, and/or strips; each depth array consisted of either 4 or 8 electrodes; each grid consisted of at least 24 contacts, and each strip at least four contacts; subjects were transferred to multiple days/nights intensive care unit (ICU) monitoring.

Electrodes and Anatomical Localization.

Depth electrodes arrays (AD-TECH MEDICAL Inc, Racine, Wis.) were 4 and 8 contact clinical depth electrode arrays consisting of a 1.3 mm diameter polyurethane shaft with Platinum/Iridium (Pt/Ir) clinical macroelectrode contacts; each contact is 2.3 mm long with 10 mm center-to-center spacing (surface area 9.4 mm2 and impedance 200-

500 Ohms). Grids and strips in medically refractory epilepsy patients are 2.5 mm diameter of exposed surface and with spacing at 1 cm from center to center on adjacent contacts. Anatomical localization of electrodes was achieved using post-implant CT data and co-registered to the patient's MRI space using normalized mutual Information. Electrode coordinates were then automatically labeled by SPM ANATOMY toolbox.

Signal Recordings.

All iEEG data were acquired with a common reference using a NEURALYNX CHEETAH electrophysiology system (9 kHz antialiasing analog filter, digitized at 32 kHz sampling rate, filtered by low pass zero phase shift 1 kHz antialiasing filter and downsampled to 5 kHz).

Clinical SOZ Localization.

The SOZ electrodes and time of seizures were determined by identifying the electrodes with the earliest iEEG seizure discharge. Seizure onset times and zones were determined by visual identification of a clear electrographic seizure discharge, followed by a look back in the iEEG recordings for the earliest electroencephalographic change contiguously associated with the seizure. A similar approach was used for identification of neocortical SOZ. These SOZ electrodes were used as the gold standard to validate rest of the analyses.

Data Pre-Processing.

Prior to analysis, continuous scalp and intracranial EEG recordings were reviewed. Channels and time segments containing significant artifacts or seizures were excluded from subsequent analysis. If an epileptiform spike was found on any channel, the data of all channels for that interval were omitted from analysis. In average, 1.3% of signal was omitted due to detected epileptiform spike activity. Furthermore, all iEEG recordings were filtered at 0 Hz and 60 Hz to remove artifacts due to DC and power-line interference.

Feature Extraction.

Figure 8D:
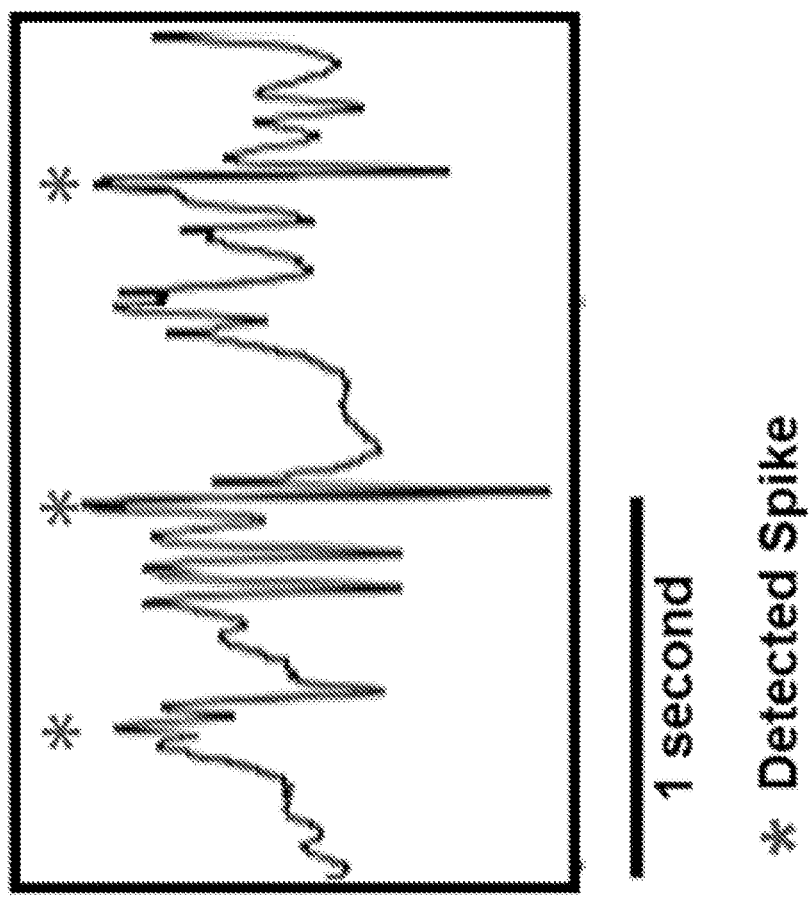
Figure 8C:
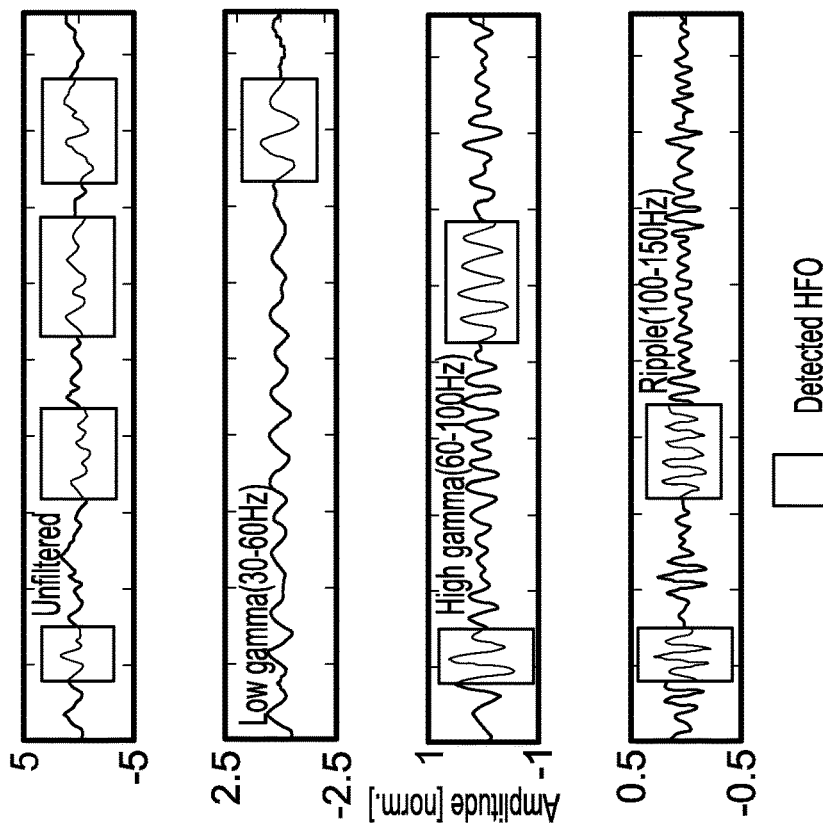

Phase-amplitude coupling (PAC) measure is extracted by correlating instantaneous phase of a low frequency signal and amplitude of a high frequency signal for a given set low and high frequency bands (FIG. 8A). In this implementation, low and high frequency contents in the signal are extracted using wavelet filters and all frequency bands are correlated against all others to create a so-called PAC-gram (FIG. 8B). Based on the observed high PAC content and existing literature, 0.1-30 Hz was chosen as the low frequency (modulating) signal and 65-115 Hz was chosen the high frequency (modulated) signal in the rest of the analysis. High-frequency oscillations (HFOs) were detected using a Hilbert transform-based technique. The data segments were bandpass filtered for every 1-Hz band step from 50 to 500 Hz. Then, the filtered-data frequency bands were normalized (z-score) and the segments where the signal amplitudes were three standard deviations above the mean for a duration of one complete cycle of a respective high frequency (50-500 Hz) were marked as HFOs (FIG. 8C). IEDs were extracted using a previously validated spike detection algorithm and detected events were stored in a database. A detection threshold of four standard deviations around the (of differential amplitude) mean was utilized to mark IEDs in this algorithm (FIG. 8D).

Analytic Scheme.

Figure 9A:
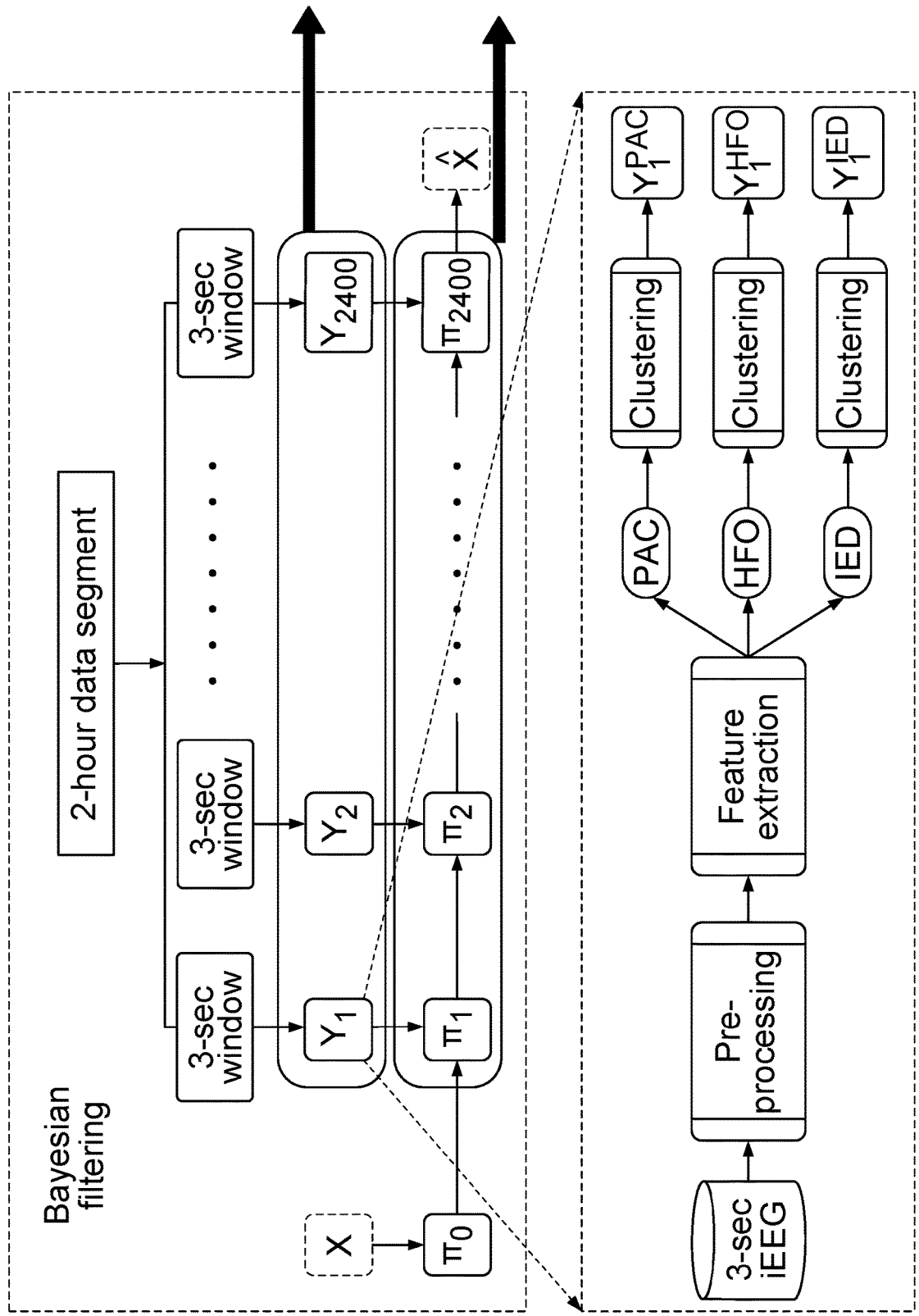
FIGS. 9A-9F show the overall analytic scheme of an example SOZ detection technique utilized in the study of example 1 and specific results from a patient.
Figure 9B:
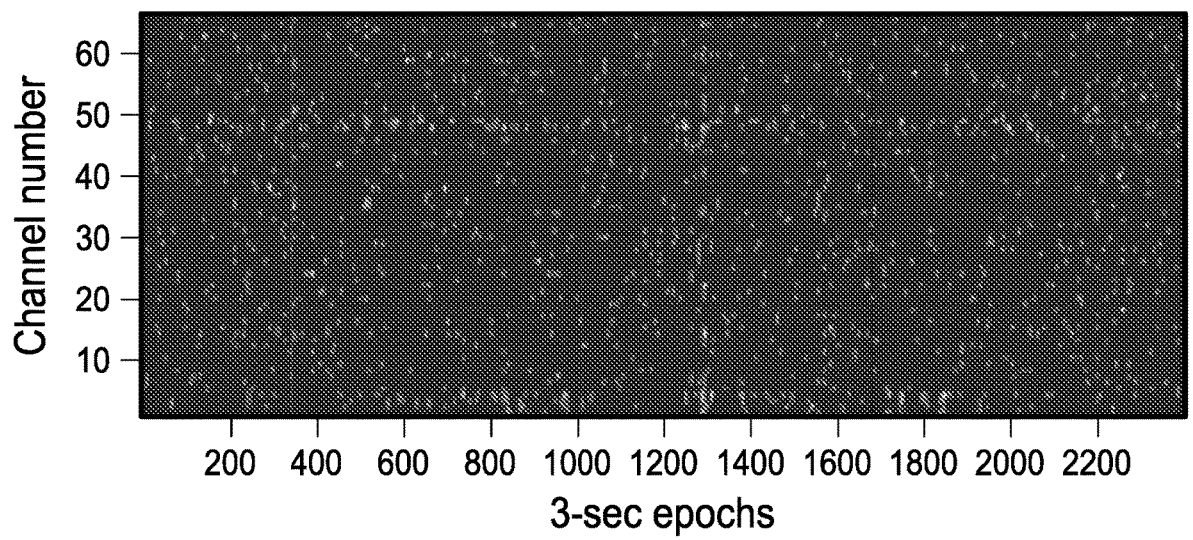
Figure 9C:
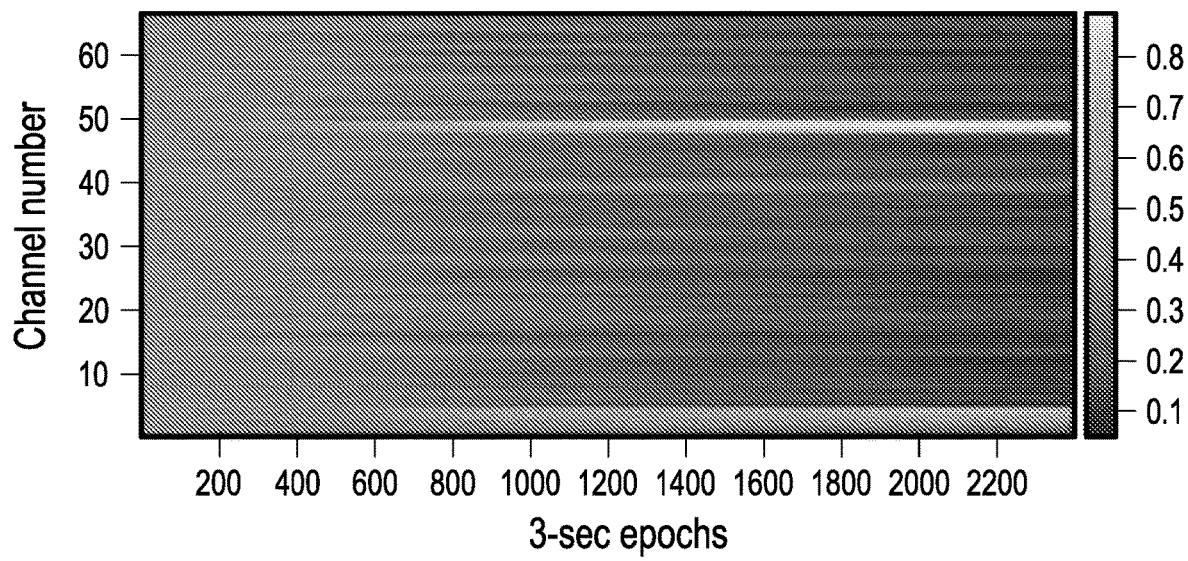
Figure 9D:
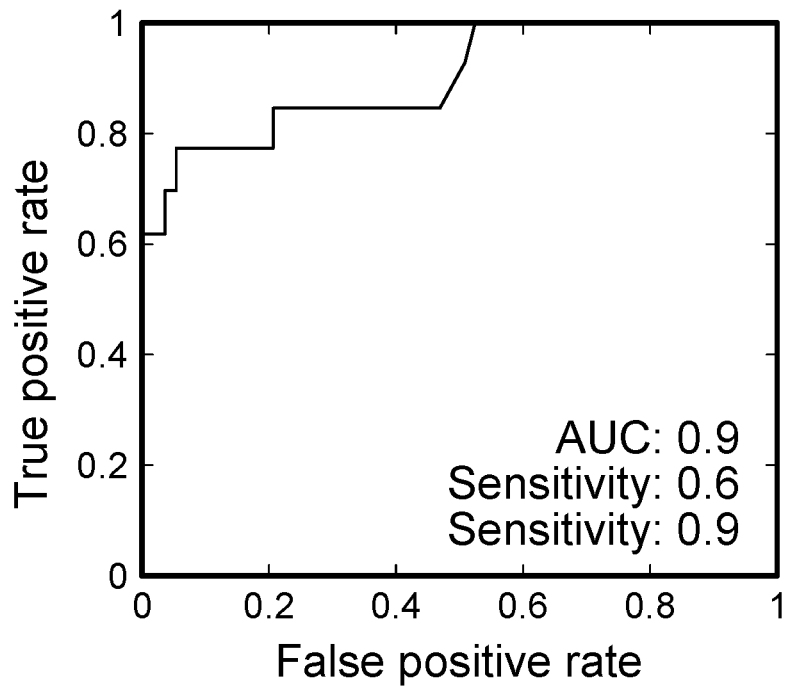
Figure 9E:
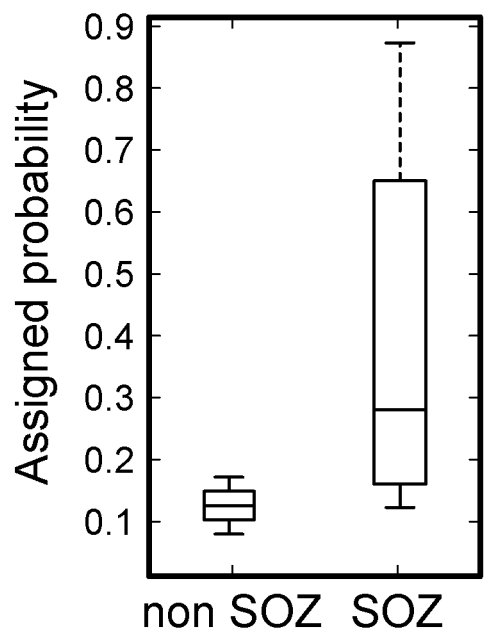
Figure 9F:
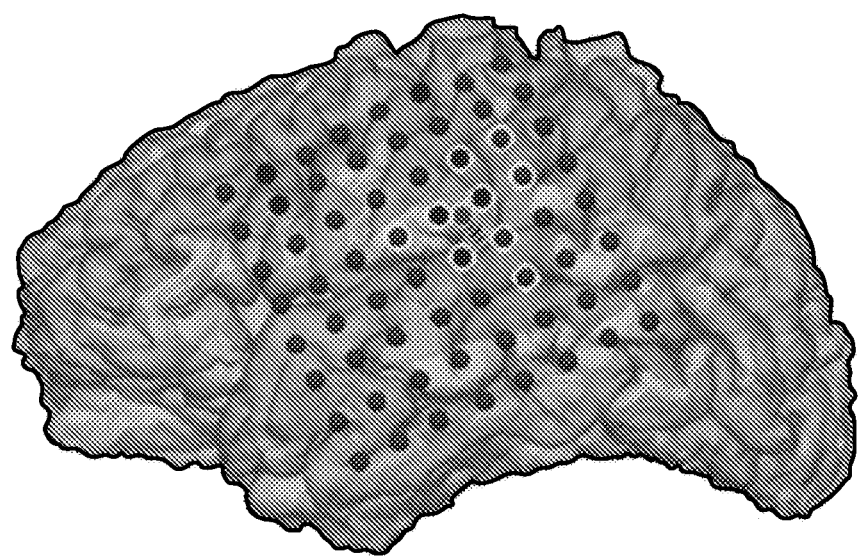
Figure 11A:
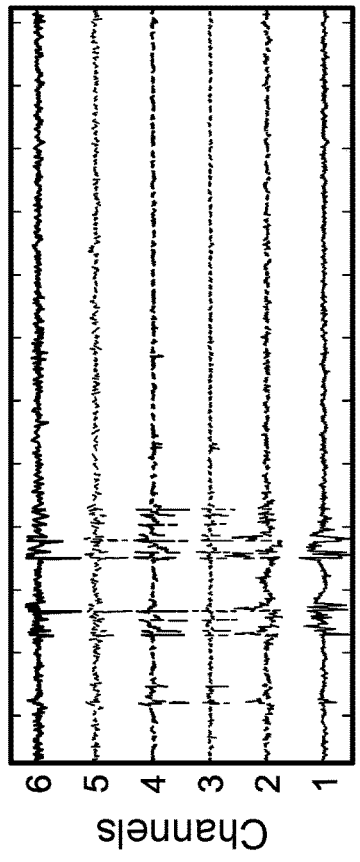
FIGS. 11A-11F show plots of a lightly supervised technique was devised to pre-select a biomarker that is better suited for localizing SOZ in a subject specific manner. Intuitively, a biomarker that best explains the signal abnormalities should be selected to achieve best performance. All subfigures are derived from a particular test subject.
Figure 11B:
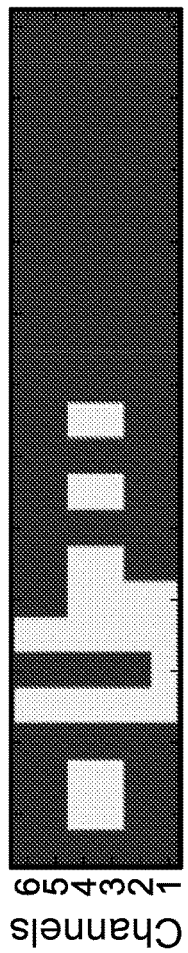

A two-hour interictal segment, sufficiently separated from seizures, was chosen for each patient to represent a monitoring duration that could be achieved during surgery. These two-hour iEEG recordings were divided into non-overlapping three-second epochs. A three-second epoch length was chosen to accommodate at least a single transient electrophysiologic event (in the form of PAC, HFO or IED) that could be associated with the seizure onset zone. PAC, HFO and IED biomarkers were extracted to measure the strength of their presence in each three-second epoch. Based on the measured strength of a biomarker in a three-second recording of a channel, a binary observation (normal or abnormal) was assigned to that channel based on a clustering algorithm. FIG. 11A illustrates the observations made from a two-hour recording of iEEG acquired using 66 channels from a selected patient. These observations made across a two-hour period were used to infer if a channel belonged to seizure onset zone, using an iterative filtering technique commonly known as Bayesian filtering. FIG. 11B shows the evolution of likelihood probabilities generated by the filtering algorithm over the same two-hour EEG segment for all electrodes. This whole process is illustrated as a flow diagram in FIG. 9A, whereas the placement of all electrodes, SOZ electrodes identified by the present method and the gold-standard SOZ electrodes for this patient are shown in FIG. 2 in 3D brain model.

Clustering.

A clustering algorithm was used to group channels into two groups (normal and abnormal) based on the strength of biomarker measured in each epoch. This step encapsulates the spatial correlation between the channels that show similar pathophysiologic activity. Apart from transient electrophysiologic events relevant to SOZs, there could also be artifacts in the form of muscle and eye artifacts or physiologic transients, which may contribute to cluster assignment. However, since the real-time filtering process sets apart the channels with consistent abnormal behavior, this artifact contribution to any SOZ determination would be minimized. Furthermore, if multiple seizure generating regions exist, it is conceivable that they would present as similar to each other but sufficiently disparate from normal brain regions; hence they would consistently be captured in the abnormal cluster.

Since all the features utilized in this study are one dimensional, Jenks natural breaks algorithm was used to find the threshold to separate normal and abnormal clusters. See Jenks, G. F., 1967. The data model concept in statistical mapping. *International yearbook of cartography,* 7(1), pp. 186-190. Since it is conceivable that a higher valued measurement of a biomarker would likely be an event associated with SOZ, the cluster with a larger cluster center value was chosen as the abnormal cluster. Channels were assigned an observation (0 or 1) based on the class they were grouped into. Furthermore, two distinct clusters may not exist in some epochs due to the absence of relevant transient electrophysiologic events. Since the clustering method finds two classes regardless, a goodness of clustering metric is defined to check the validity of the clustering result. The goodness of clustering metric is defined as the quantity $$G = \frac{S - S_C}{S},$$

where S denotes the sum of squared distances of all the data points from their mean and $S_c$ denotes the sum of squared distances of the data points from their respective cluster centers. G ranges between [0,1] with 0 indicating bad and 1 indicating good clustering. In the present method, the clusters are regarded as valid clusters only when the condition G>0.5 is met.

Bayesian Filtering.

A Bayesian filters is used to estimate the present state of a dynamic system based on noisy real-time measurements. This form of belief propagation takes a system's previous states and current observation into account and estimates a plausible present state. Hence, this technique is able to utilize the repetitive nature of abnormal transient events while determining SOZ channels. With certain assumptions, it is possible to estimate the present state of the system using the previous state estimate and current observation.

Suppose that inter-ictal iEEG data is recorded from a patient through M channels. Initially, this data is discretized by dividing the recording duration into N epochs. Each channel has a true state X(k), taking values in [0,1]. The system interprets the event {X(k)=0} as channel k not being in the SOZ and the event {X(k)=1} as channel k being in the SOZ. Based on the observation at epoch n, channel k is assigned a value $Y_n(k)$, taking values in {0,1} with 0 and 1 representing normal and abnormal events respectively. The study also denotes the observation of channel k from epoch 1 to n as $Y_1^n(k)$. It can be shown that the likelihood of {X(k)=1} after observing channel k for n continuous epochs, denoted as $\pi_n(k)$, is given as $$\pi_n(k) = \frac{(1-\theta)\pi_{n-1}(k)\lambda^{Y_n(k)}}{(1-\theta)\pi_{n-1}(k)\lambda^{Y_n(k)} + (1+\theta)(1-\pi_{n-1}(k))\lambda^{-\lambda_n(k)}}$$

Where $\pi_{n-1}(k)$ denotes the belief at epoch n−1, $\theta \in [0,1]$ denotes the expected bias of channel k for being in SOZ and λ is the likelihood ratio defined as $$\frac{1+\theta}{1-\theta}.$$

Results.

The study investigated the contributions of PAC, HFO rate and inter-ictal epileptiform discharges (IED) rate as features in determining SOZ using the filtering process involving feature clustering and Bayesian filtering. First, these biomarkers were extracted in the three-second epochs and observations were assigned to all the channels based on the clustering result. Second, these observations were utilized in the Bayesian filter model to iteratively update the likelihood of a channel being in the SOZ. Third, the likelihood probabilities at the end of the filtering process were compared against clinician-determined SOZ to plot ROC curves and thus evaluate the combined efficacy of a particular biomarker and the method. In order to understand the separate contributions of the filtering process in addition to the biomarkers, the study performed another experiment. In this experiment, biomarkers were extracted in the three-second epochs and these measures were summed over 2400 epochs to generate likelihoods of the channels being in SOZ. Likelihood probabilities were generated by normalizing the likelihoods resulted from this process. ROC curves were plotted in a similar manner to evaluate this approach. The Area Under ROC curve (AUC) metrics for all the analyzed subjects are listed in Table 1 columns 6-11 for PAC, PAC with Bayesian filter, HFO, HFO with Bayesian filter, IED and IED with Bayesian filter respectively. See FIGS. 10A-C and 12A-D.

Figure 10C:
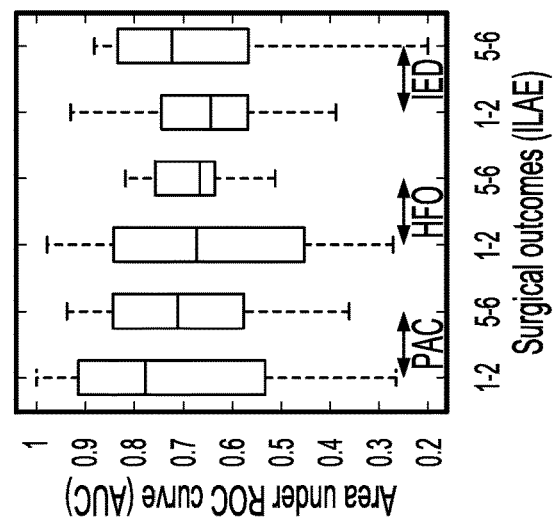
FIG. 10C shows a comparison between obtained AUCs and surgical outcomes (ILAE). Our SOZ detection algorithm, on average, was not quite successful in the patients who had bad outcomes. This observation is quite prominent with PAC biomarker and not so much in the other biomarkers.
Figure 10B:
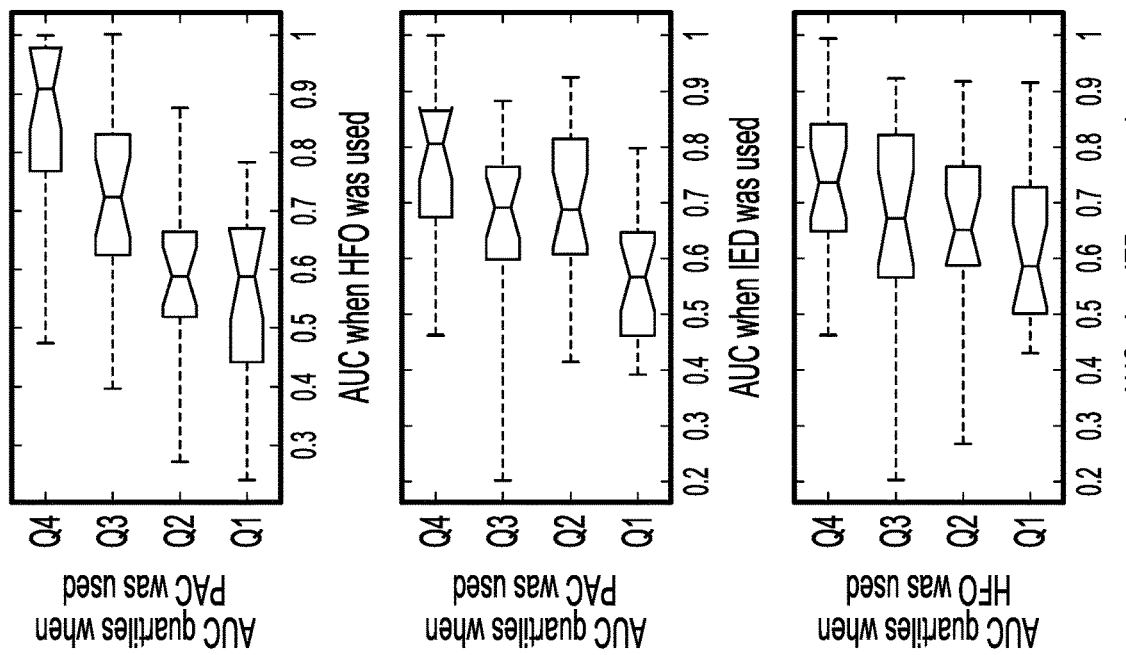
FIG. 10B shows a cross comparison between the AUCs obtained with different biomarkers using a quartile analysis. Overall, there is noticeable correlation between the AUCs of different biomarkers. AUCs obtained using PAC were significantly different than HFOs (p=0.0002) and IEDs (p=0.0006) while the AUCs obtained using HFOs and IEDs were similar (p=0.76).
Figure 10A:
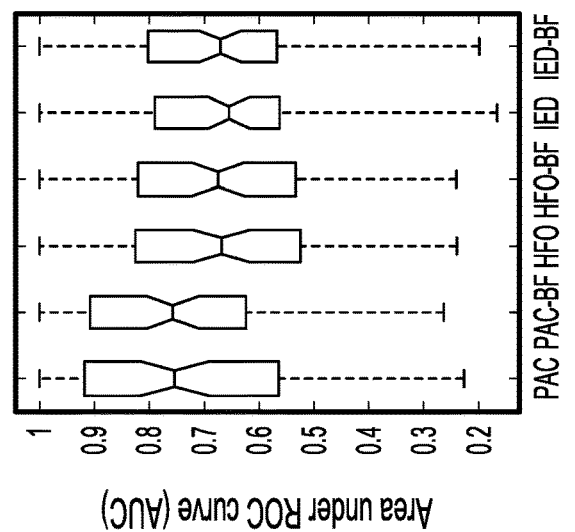

The study tested the statistical significances of the different results using a two-tailed paired t-test, whose results are shown in FIG. 10A. Overall, PAC was, on average, significantly better than other conventional biomarkers in interictally localizing SOZ (7% higher AUC). Whereas, although Bayesian filter based algorithm slightly improved the AUCs with HFOs and IEDs, the improvement was prominent particularly when it was utilized with PAC. Furthermore, the study involved statistical tests to compare the AUCs obtained using the different biomarkers whose results are shown in FIG. 10B. Based on the statistical tests, it appears that the AUCs obtained using the three biomarkers possess a consistent trend; i.e., the patients whose SOZs were most accurately localized by a biomarker X, also obtained very high accuracies when evaluated with other biomarkers. Regardless, the AUCs obtained using PAC were significantly different than those obtained using HFOs or IEDs as biomarkers (p-value 0.0001, 0.0005) and the AUCs obtained using HFOs and IEDs showed significant correlation, which is resembled in the p-value measure of 0.76 for a two-tailed paired t-test. Apart from this, the study also evaluated the correlation between disagreements with the gold standard and surgical outcomes based on ILAE scores. In other words, a significant correlation between lower AUCs and higher ILAE scores would mean that there are additional channels which might have been in the SOZ but not resected. The study evaluated this by comparing the AUCs for the groups of patients who had excellent and significantly worsened surgical outcomes. FIG. 10C shows the ranges of AUCs obtained for the groups of patients who had ILAE scores of 1, 2 (excellent outcomes) and 5, 6 (worsened outcomes). An inverse correlation between AUCs and surgical outcomes observed with PAC suggests that using PAC biomarker to detect SOZ might provide an alternative or complementary information to assist epilepsy surgery. However, HFO and IED did not show any significant correlation between AUCs and surgical outcomes.

Figure 11C:
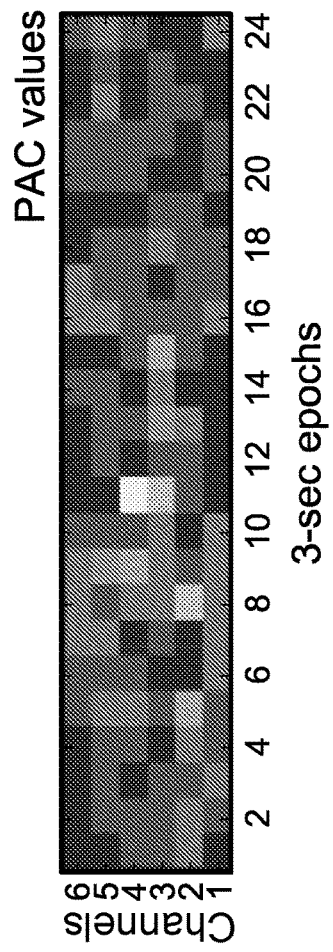
Figure 11D:
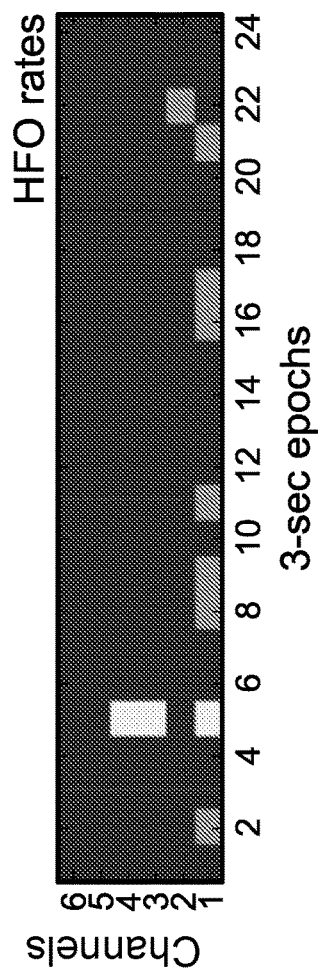
Figure 11E:
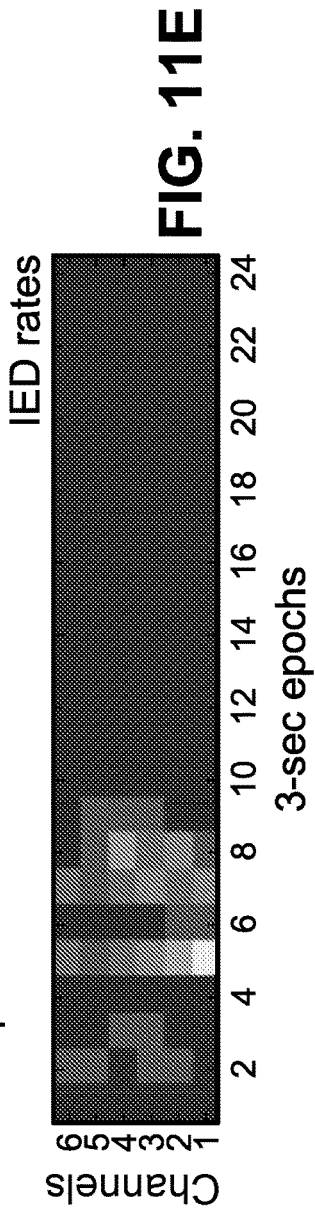
Figure 11F:
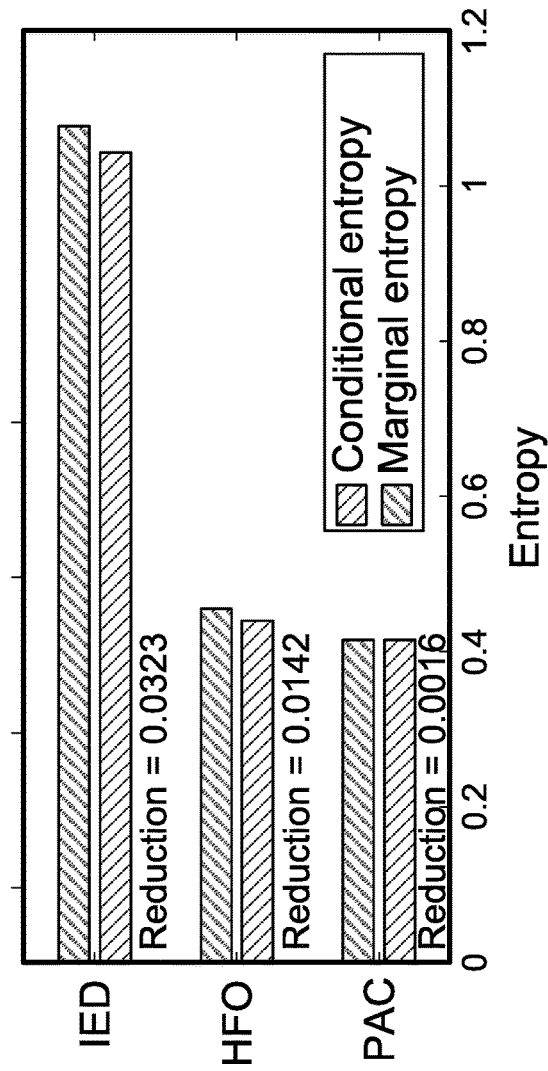

Pre-selection of patient specific electrophysiologic biomarkers. It is evident from the table that extends across FIGS. 12A-D that investigated biomarkers may not be universally applicable for the task of interictal SOZ localization. Knowledge of the ground truth is required in order to select a patient-specific biormarker. Since this knowledge is not generally available at the time of electrode implantation, this is an extremely difficult problem. Here the study describe a partly supervised technique, which can achieve this with minimal expert supervision and moderate accuracy. A group of nine patients was selected to demonstrate this technique, which consists of three subgroups (three patients in each subgroup), for whom different biomarkers (PAC, HFO and IED) provided the best accuracy in SOZ localization. A short iEEG recording (approximately 1 minute long), at the beginning of the analysis segment used in the prior analysis, was chosen for each patient and transient electrophysiological events were annotated for every three-second epoch in the chosen recording. FIG. 11A shows the recording selected for patient 458 with few transient electrophysiological events, which are annotated in FIG. 11B. PAC, HFO rate and IED rate measures were calculated in the three-second epochs resembling the present original methodology. An example is shown in FIGS. 11C, 11D, and 11E, which display the features PAC, HFO and IED extracted for the recording showed in FIG. 11A. The marginal entropies and conditional entropies (conditioned on the annotations) were calculated, for each biomarker within this short recording. A large reduction in the conditional entropy of a biomarker would mean that this biomarker explains the annotations better than the other biomarkers. From the table of FIGS. 12A-D, IEDs provided the best AUC for the case of patient 458. FIG. 11F, which shows the reductions in conditional entropy for the three biomarkers investigated, also concurs with result as IED obtained the largest reduction. This analysis was performed for the selected nine patients, the results of which are reported in the table of FIG. 13. This method is able to correctly identify the best suited biomarker for six out of nine patients indicating that pre-selection of patient specific biomarkers could be feasible in large scale.

Discussion

The current study describes the results from use of an unsupervised algorithm which utilizes Bayesian Filtering, feature clustering, and multiple feature input of iEEG data with clinical hardware configurations. The study verified the correlation of the present algorithm's outputs and SOZ, and assessed the feasibility using this algorithm to locate SOZ during mixed sleep/wake behavioral states in patients with temporal and extratemporal lobe epilepsy. The results of the present study indicate that the utilization of Bayesian Filtering of iEEG and unsupervised clustering is capable of identifying the SOZ in an efficient manner, and could be employed for automatic or semi-automated SOZ localization in clinical practice.

The study evaluated High Frequency Oscillations as a feature to capture the most widely used inter-ictal biomarkers of epileptic brain, as well as older biomarkers (Interictal Epileptiform Discharges) and newer (phase amplitude coupling). The results of the present study indicate that the integration of spectral characteristics of the iEEG and unsupervised clustering along with Bayesian filtering could be employed for automatic SOZ localization in a clinical setting. The study analyzed human iEEG data recorded using a high sampling acquisition platform, the study was able to reliably identify SOZ using the present approach, supporting the assumption that the individual biomarkers provided as input are good indicators for the epileptogenic zone. When the spatial distribution of the entire feature group was used, a SOZ identification accuracy with AUC of 0.76 for Bayesian filtered PAC was observed.

The Prognostic Value of Bayesian Filtering of iEEG and Multiple Features

Using 120 min baselines and PI data, the algorithm satisfactorily localized SOZ in 75 of 82 patients (defined by AUC>0.6 with at least one of the utilized features), and localized with greater than 0.7 AUC in 64 of 82 patients, where it can be taken to mean that spatial distribution was closely overlapped with the electrodes that were placed over the regions where the seizures were thought to originate per epileptologist evaluation, suggesting the good prognostic value of this automated technique. Bayesian Filtering improved localization potential in at least one feature in all but 7 patients. Additionally, utilization of Bayesian filter is more likely to be useful when there is inherent randomness in the observations, than in a situation where the observations are less random. This is revealed in the present results where the impact of using Bayesian filter was significant when used with PAC and not so with HFO and IED. In this study, utilized PAC measurements were real valued and HFO and IED measurements were discrete valued (HFO and IED rates).

Although various implementations have been described in detail above, other modifications are possible. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A computer-implemented method, comprising:
    obtaining, by a computing system, and for each of a plurality of sensor channels, a respective set of electroencephalogram (EEG) data for the sensor channel over a first interictal time interval, each sensor channel corresponding to a different one of a plurality of EEG sensors disposed at different locations of a brain of a mammal;
    segmenting, by the computing system, and for each of the plurality of sensor channels, the respective set of EEG data for the sensor channel into a plurality of EEG data segments, each EEG data segment corresponding to one of a plurality of sub-intervals of the first interictal time interval;
    for each sensor channel of the plurality of sensor channels and each of the plurality of sub-intervals:
        (a) generating, based on analysis of the EEG data segment for the sub-interval, a current classification of the sensor channel at the sub-interval as either (i) a non-epileptogenic sensor channel for an EEG sensor that is likely not disposed at or near an epileptogenic region of the brain, or (ii) an epileptogenic sensor channel for an EEG sensor that is likely disposed at or near an epileptogenic region of the brain; and
        (b) using the current classification of the sensor channel at the sub-interval to update a Bayesian metric for the sensor channel, the Bayesian metric determined based on the current classification of the sensor channel at the sub-interval and classifications of the sensor channel from any preceding sub-intervals in the first interictal time interval, the Bayesian metric indicating a long-term classification of the sensor channel expressed as a cumulative belief that the sensor channel is either a non-epileptogenic sensor channel or an epileptogenic sensor channel; and
    providing, by the computing system, and for each of one or more of the plurality of sensor channels based on the Bayesian metric for the sensor channel, an indication of whether the sensor channel has an EEG sensor that is likely disposed at or near an epileptogenic region of the brain.

2. The computer-implemented method of claim 1, wherein a total number of sensor channels in the plurality of sensor channels is in the range 14 through 512.

3. The computer-implemented method of claim 1, wherein a total length of the first interictal time interval is in the range 1 minute through 120 minutes.

4. The computer-implemented method of claim 1, wherein a total length of each sub-interval in the plurality of sub-intervals is in the range 3 seconds through 30 seconds.

5. The computer-implemented method of claim, 1, wherein all of the sub-intervals in the plurality of sub-intervals have an equal length.

6. The computer-implemented method of claim 1, wherein the plurality of EEG sensors are intracranial EEG sensors.

7. The computer-implemented method of claim 1, wherein the mammal is a human.

8. The computer-implemented method of claim 1, wherein for each sensor channel of the plurality of sensor channels, generating the current classification of the sensor channel at each of the plurality of sub-intervals comprises:
    determining whether the EEG data segment for the sub-interval indicates occurrence of a transient event;

if the EEG data segment for the sub-interval does not indicate occurrence of a transient event, classifying the sensor channel as a non-epileptogenic sensor channel for the sub-interval; and
if the EEG data segment for the sub-interval indicates occurrence of a transient event, classifying the sensor channel as an epileptogenic sensor channel for the sub-interval.

9. The computer-implemented method of claim 1, wherein for each sub-interval of the plurality of sub-intervals, generating the respective current classifications of the plurality of sensor channels comprises:
for each sensor channel of the plurality of sensor channels, determining values for one or more features of the EEG data segment that corresponds to the sub-interval and the sensor channel;
based on the values for the one or more features of the EEG data segments that correspond to the sub-interval, clustering the plurality of sensor channels into multiple clusters of sensor channels;
setting the respective current classifications of the sensor channels in a first subset of the multiple clusters to identify these sensor channels as non-epileptogenic sensor channels for the sub-interval; and
setting the respective current classifications of the sensor channels in a second subset of the multiple clusters to identify these sensor channels as epileptogenic sensor channels for the sub-interval.

10. The computer-implemented method of claim 9, wherein the one or more features of the EEG data segment comprise at least one of power-in-bands, high-frequency oscillation, inter-ictal spikes, phase amplitude coupling.

11. The computer-implemented method of claim 1, further comprising determining boundaries of an epileptogenic region of the brain using indications of which sensor channels of the plurality of sensor channels have EEG sensors that are likely disposed at or near the epileptogenic region of the brain.

12. The computer-implemented method of claim 1, wherein an epileptogenic region of the brain that is located using indications of which sensor channels of the plurality of sensor channels have EEG sensors that are likely disposed at or near the epileptogenic region of the brain is resected.

13. The computer-implemented method of claim 1, further comprising using indications of which sensor channels of the plurality of sensor channels have EEG sensors that are likely disposed at or near the epileptogenic region of the brain to select a subset of the plurality of sensor channels to monitor during a process that is to predict occurrence of an epileptic event.

14. The computer-implemented method of claim 13, wherein the epileptic event is a seizure.

15. The computer-implemented method of claim 1, wherein the plurality of sub-intervals span an entirety of the first time interval.

16. The computer-implemented method of claim 1, wherein the providing occurs after having iteratively updated the Bayesian metric for all the sub-intervals in the plurality of sub-intervals.

17. The computer-implemented method of claim 1, wherein for each sensor channel of the plurality of sensor channels, generating the current classification of the sensor channel at each of the plurality of sub-intervals comprises determining whether the EEG data segment belongs to a first cluster of EEG data segments or a second cluster of EEG data segments, the first cluster of EEG data segments comprising EEG data segments from a first subset of the plurality of sensor channels grouped by values of one or more EEG waveform features, the second cluster of EEG data segments comprising EEG data segments from a second subset of the plurality of sensor channels grouped by values of the one or more EEG waveform features.

18. The computer-implemented method of claim 1, wherein for each sensor channel of the plurality of sensor channels, the Bayesian metric for the sensor channel is updated at each of the plurality of sub-intervals using the current classification of the sensor channel at the sub-interval and an expected bias for the sensor channel.

19. A computing system comprising:
one or more processors; and
one or more non-transitory computer-readable media having instructions stored thereon that, when executed by the one or more processors, cause performance of operations comprising:
obtaining, for each of a plurality of sensor channels, a respective set of electroencephalogram (EEG) data for the sensor channel over a first interictal time interval, each sensor channel corresponding to a different one of a plurality of EEG sensors disposed at different locations of a brain of a mammal;
segmenting, for each of the plurality of sensor channels, the respective set of EEG data for the sensor channel into a plurality of EEG data segments, each EEG data segment corresponding to one of a plurality of sub-intervals of the first interictal time interval;
for each sensor channel of the plurality of sensor channels and each of the plurality of sub-intervals:
(a) generating, based on analysis of the EEG data segment for the sub-interval, a current classification of the sensor channel at the sub-interval as either (i) a non-epileptogenic sensor channel for an EEG sensor that is likely not disposed at or near an epileptogenic region of the brain, or (ii) an epileptogenic sensor channel for an EEG sensor that is likely disposed at or near an epileptogenic region of the brain; and
(b) using the current classification of the sensor channel at the sub-interval to update a Bayesian metric for the sensor channel, the Bayesian metric determined based on the current classification of the sensor channel at the sub-interval and classifications of the sensor channel from any preceding sub-intervals in the first interictal time interval, the Bayesian metric indicating a long-term classification of the sensor channel expressed as a cumulative belief that the sensor channel is either a non-epileptogenic sensor channel or an epileptogenic sensor channel; and
providing, for each of one or more of the plurality of sensor channels based on the Bayesian metric for the sensor channel, an indication of whether the sensor channel has an EEG sensor that is likely disposed at or near an epileptogenic region of the brain.

* * * * *